United States Patent
Künnecke

(10) Patent No.: US 10,022,081 B2
(45) Date of Patent: Jul. 17, 2018

(54) SAMPLING DEVICE AND SAMPLING METHOD

(75) Inventor: Wolfgang Künnecke, Braunschweig (DE)

(73) Assignee: TRACE ANALYTICS, GMBH, Braunschweig (DE)

( * ) Notice: Subject to any disclaimer, the term of this patent is extended or adjusted under 35 U.S.C. 154(b) by 932 days.

(21) Appl. No.: 13/256,184

(22) PCT Filed: Mar. 10, 2010

(86) PCT No.: PCT/EP2010/053052
§ 371 (c)(1),
(2), (4) Date: Nov. 28, 2011

(87) PCT Pub. No.: WO2010/103051
PCT Pub. Date: Sep. 16, 2010

(65) Prior Publication Data
US 2012/0071788 A1    Mar. 22, 2012

(30) Foreign Application Priority Data

Mar. 10, 2009  (DE) .................. 10 2009 001 455
Mar. 3, 2010   (WO) ................ PCT/EP2010/052727

(51) Int. Cl.
| A61B 5/153 | (2006.01) |
| A61B 5/145 | (2006.01) |
| A61B 5/00  | (2006.01) |
| A61B 5/15  | (2006.01) |

(52) U.S. Cl.
CPC .......... *A61B 5/153* (2013.01); *A61B 5/14503* (2013.01); *A61B 5/14525* (2013.01); *A61B 5/14546* (2013.01); *A61B 5/15003* (2013.01); *A61B 5/150229* (2013.01); *A61B 5/150366* (2013.01); *A61B 5/150389* (2013.01); *A61B 5/150503* (2013.01); *A61B 5/415* (2013.01); *A61B 5/150755* (2013.01)

(58) Field of Classification Search
CPC ............ A61B 5/14525; A61B 5/14528; A61B 5/14503; A61B 5/14546; A61B 5/150389
USPC ........................................................ 600/573
See application file for complete search history.

(56) References Cited

U.S. PATENT DOCUMENTS

| | | |
|---|---|---|
| 3,640,269 A | 2/1972 | Delgado |
| 4,008,717 A | 2/1977 | Kowarski |
| 4,221,567 A | 9/1980 | Clark et al. |
| 4,265,249 A | 5/1981 | Schindler et al. |
| 4,685,463 A * | 8/1987 | Williams ........... A61B 5/14528 600/365 |
| 4,694,832 A | 9/1987 | Ungerstedt |
| 5,640,954 A * | 6/1997 | Pfeiffer .............. A61B 5/14528 600/345 |

(Continued)

FOREIGN PATENT DOCUMENTS

| | | |
|---|---|---|
| DE | 4426694 A1 | 2/1996 |
| GB | 2100859 A | 6/1982 |

(Continued)

*Primary Examiner* — Rene Towa
*Assistant Examiner* — H. Q. Nguyen
(74) *Attorney, Agent, or Firm* — Duane Morris LLP; J. Rodman Steele, Jr.; Gregory M. Lefkowitz

(57) ABSTRACT

The present invention relates to a sampling device, a sampling system and a method of sampling, and in particular a method of analysis, for application to a living entity.

18 Claims, 15 Drawing Sheets

(56) References Cited

U.S. PATENT DOCUMENTS

| | | | |
|---|---|---|---|
| 6,632,315 B2 | 10/2003 | Liska et al. | |
| 6,811,542 B2 | 11/2004 | Liska et al. | |
| 6,852,500 B1 | 2/2005 | Hoss et al. | |
| 7,162,290 B1 | 1/2007 | Levin | |
| 7,455,657 B2 * | 11/2008 | Naimark | A61M 5/142 604/523 |
| 2005/0209518 A1 * | 9/2005 | Sage et al. | 600/366 |
| 2006/0135917 A1 * | 6/2006 | Reihl et al. | 604/272 |
| 2007/0287952 A1 * | 12/2007 | Shah | A61B 5/145 604/27 |
| 2008/0097288 A1 | 4/2008 | Levin et al. | |

FOREIGN PATENT DOCUMENTS

| | | |
|---|---|---|
| WO | 199945982 A3 | 9/1999 |
| WO | 200106928 A1 | 2/2001 |
| WO | 200110483 A3 | 2/2001 |
| WO | 2004032735 A3 | 4/2004 |
| WO | 2008059050 A3 | 5/2008 |

* cited by examiner

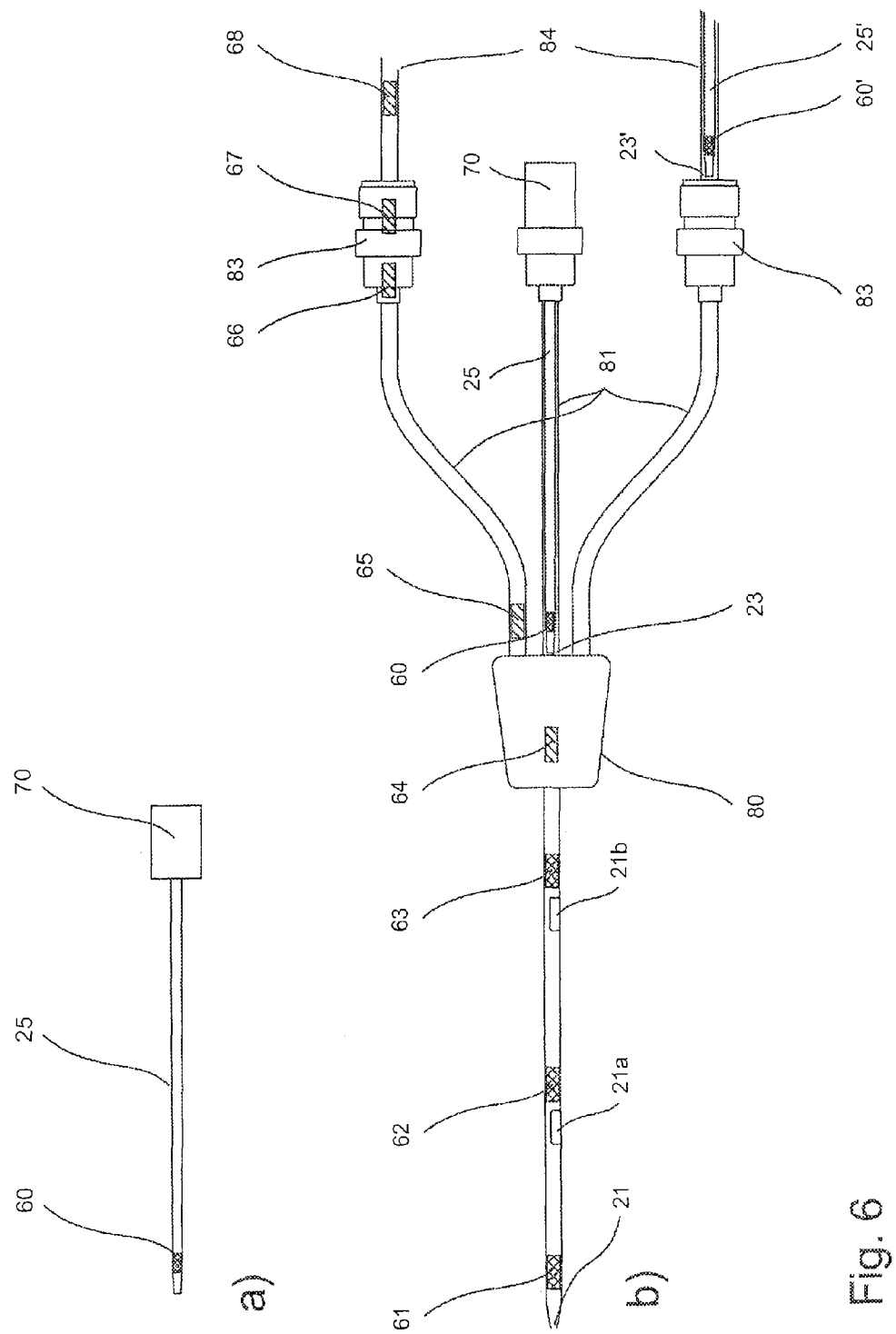

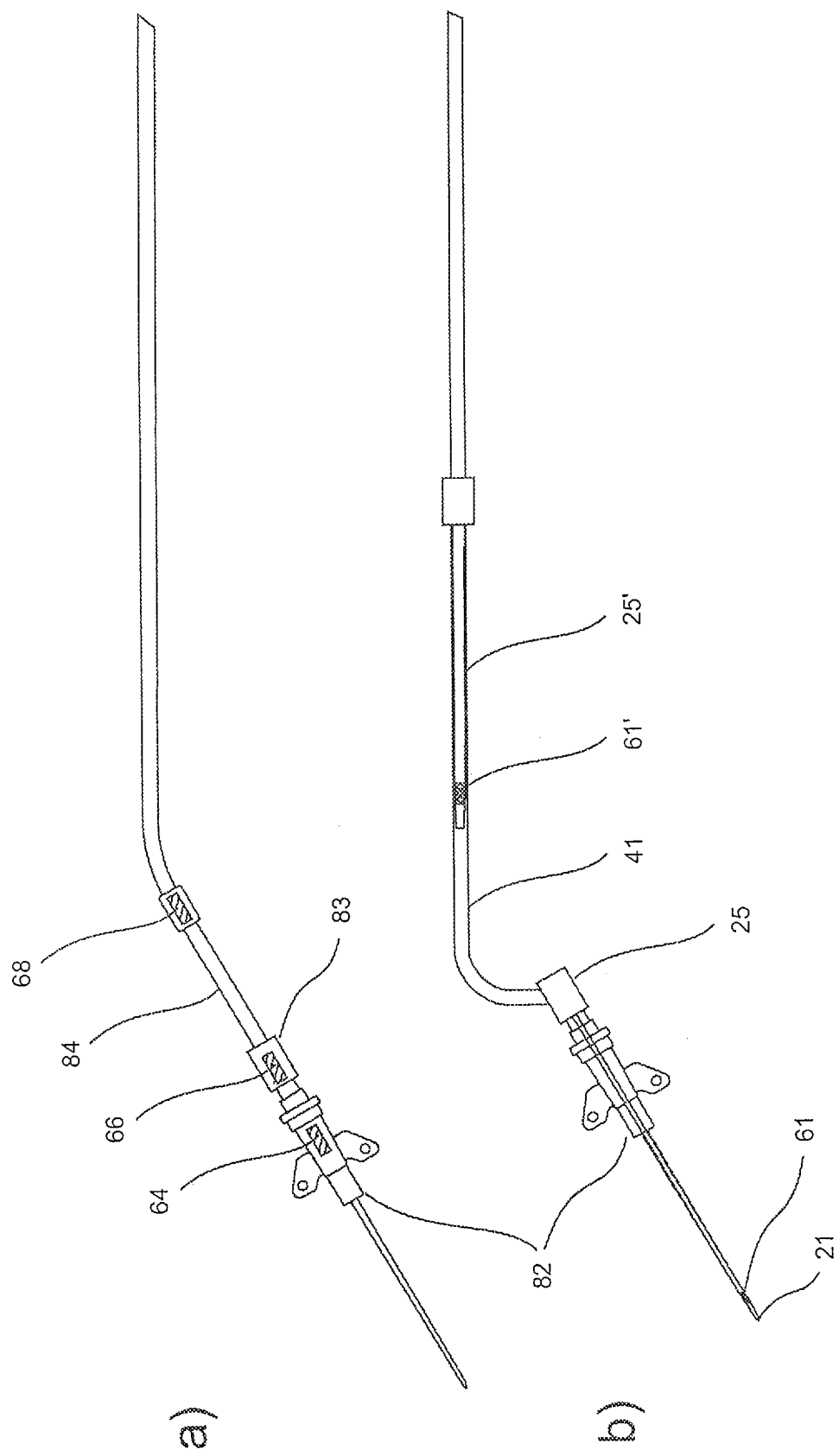

SAMPLING DEVICE AND SAMPLING METHOD

CROSS-REFERENCE TO RELATED APPLICATIONS

This application is a § 371 national stage entry of International Application No. PCT/EP2010/053052, filed Mar. 10, 2010, which claims priority to German Patent Application No. DE 10 2009 001 455.1, filed Mar. 10, 2009 and PCT/EP2010/052727, filed Mar. 3, 2010, the entire contents of which are incorporated herein by reference.

FIELD OF THE INVENTION

The present invention relates to a sampling device, a sampling system and a method of sampling, and in particular to a method of analysis, for application to a living entity.

BACKGROUND OF THE INVENTION

The invention relates to the field of determining the presence and/or concentration of an analyte in a medium intended for sampling. Determination requirements of this kind occur particularly in the continuous or discontinuous monitoring of metabolic processes in a living entity such for example as a human being, in biotechnical cultivation and in other technical processes. What is desired in each of these cases is for the determination of the analyte, or in other words its presence and/or concentration in the medium being sampled, to be as prompt and as accurate as possible, without at the same time causing any interference with the medium intended for sampling or with the processes that may possibly be taking place in it and without any major amounts of the medium being consumed for the purposes of the analysis.

The invention will be described below chiefly in relation to applications to the bodies of human beings or animals, and in particular in relation to requirements in medical analysis. However, the invention is not limited to this field. Hence, where terms drawn from the medical field such for example as cannula or catheter are used, what these terms are also understood to mean, as further embodiments, are corresponding articles used in the chemical and biotechnology industries, such for example as tubes and flexible lines.

The determination of an analyte in a medium is usually performed by bringing a sensor suitable for the given analyte into direct contact with the medium intended for examination itself or with a sample of the medium that has been taken from the main body of the medium. In this way, in medical analysis for example, attempts are made to arrange miniaturized sensors directly in a patient and, when this is done, preferably in his blood stream. The given sensor is then intended to determine one or more assigned analytes continuously or at a preselected point in time, i.e. to ascertain its/their presence and/or concentration in the medium and to make the result of this ascertainment accessible in some suitable form, as an electrical signal for example or as a visual signal or a radio signal. It is a problem in this case that it is only with difficulty that a sensor arranged inside a patient, such for example as an implanted sensor or one situated in the blood stream, can be calibrated, because to do this a calibrating medium has to be introduced into the patient in such a way that it displaces any medium belonging to the body at the sensor's location to such an extent that any falsification of the calibration by effects coming from outside the calibrating medium can be largely or entirely ruled out. This is a very complicated process and because of the risk that it involves of an incursion into the patient it is impossible in many cases.

In medical analysis, attempts are therefore also made to obtain a sample of a medium from the patient, such as a blood sample for example, continuously or at a preselected point in time by fitting a sampling access to the patient. This sample is then conveyed to a sensor and is then discarded or fed back to the patient. It is particularly desirable for the sample to be fed back in order not to put the patient under unnecessary stress by the repeated taking of samples, in that this would, as it were, exsanguinate him. Hence, in the methods of analysis that have been described, the obtaining of a sample means that the sensor is no longer situated directly in the main body of the medium intended for analysis but in the sampling access, such as in a catheter or cannula for example, and analyses a sample of the medium that flows into, or that has flowed into, or that has been drawn by suction into, the sampling access. The sensor may equally well be arranged at an even greater distance from the main body of the medium, such for example as at an end of the sampling access remote from the main body of the medium. And finally, the sensor may even be totally separated from a fluid-carrying means of communication with the main body of the medium, such for example as by feeding a blood sample that has been isolated to an external sensor such as a test strip.

Where sensors are not arranged within the main body of the medium, it must be remembered that the characteristics of the medium intended for sampling may be altered simply by the taking of the sample from the main body of the medium. In this way, a blood sample for example that is drawn out quickly through a cannula may be subjected to high shear forces, which may result in damage-induced artifacts. Another cause for concern is that blood samples in particular clot. Clotting of this kind may for example take place even within a cannula or an indwelling venous catheter. This needs to be prevented not only to ensure that sensor signals are meaningful but also to stop thrombuses from being introduced into the patient.

In continuous-flow methods of medical analysis, it is often necessary for the sample intended for analysis to be left to stand in a measuring cell for a certain contact time, because flows and pulsations caused for example by the heart beat or by fluctuations in blood pressure may affect sensors.

Attempts have therefore been made to decouple the sensor and the medium intended for sampling from one another by interposing a transporting medium. In this case, the transporting medium is first brought into contact with the medium intended for analysis in order to charge the transporting medium with the analyte or analytes. The analyte-charged sample of the transporting medium is then transported to the sensor and measurements are made on it there. What is advantageous about methods of this kind is that by the interposing of a transporting medium it becomes possible for the conditions, such as pressure and temperature for example, prevailing at the sensor to be preselected and for them to be more accurately controlled than they can be in the medium intended for analysis. If the method is carried out in a suitable way, it is also possible to avoid any noticeable volume of material whatever being taken from the main body of the medium.

An example of methods of this kind is methods of dialysis. In them a probe is introduced into the medium to be examined and if necessary is implanted for a protracted period, the probe containing a transporting medium that, via a measuring window covered with a dialysis membrane or gas-diffusing membrane, is brought into metabolic communication with the medium intended for examination. The probe is flushed with the transporting medium continuously or in pulses. Through the membrane and the measuring window, the analyte enters the transporting medium in an analyte receiving chamber situated downstream of the membrane in the direction of flow of the analyte, and is transported out of the probe through a probe outlet and out of the region occupied by the medium to be examined, which region may in particular be a bioreactor or the body of a human or an animal. Examples of such probes and associated methods of sampling are described in DE 44 26 694, U.S. Pat. No. 3,640,269, U.S. Pat. No. 4,008,717, U.S. Pat. No. 4,221,567, U.S. Pat. No. 4,694,832, U.S. Pat. No. 6,632,315, U.S. Pat. No. 6,811,542, U.S. Pat. No. 6,852,500, U.S. Pat. No. 7,162,290, US 2008-97288, WO 99/45982 A2, WO 01/06928 A1, WO 2004/032735 A2, WO 2001/010483 A1 and WO 2008/059050 A2.

Precisely when the probe is arranged in the body of a living entity, and in particular in the body of a human or animal, the concentration of the analytes transported out of the probe may fluctuate widely in the transporting medium regardless of their concentration in the body of the living entity. The inventors suspect that the membrane closing off the measuring window comes into contact with tissue or other solid matter forming part of the living entity due to movements of the living entity and when this happens becomes partly or completely covered in such a way that passage of the analyte into the analyte receiving chamber is hampered. The inventors have also found that the concentration of the analyte in the transporting medium very much depends on the flow rate of the medium intended for analysis, and in particular on the flow rate of blood.

A further disadvantage is that, due to their small outside diameter, conventional microdialysis probes become awkwardly flexible as their length increases. Microdialysis probes need to be about 30 cm long to enable them to be inserted into, or rather through, the inner lumen of a central venous catheter. Long microdialysis probes of this kind are difficult to insert into a catheter against the stream of blood flowing out, which makes the microdialysis probe more difficult to operate and encourages damage to the probe, as a result of kinking for example. Even comparatively short microdialysis probes of a length of 10 cm for example, for use in a conventional indwelling venous catheter, can be threaded in only with a great deal of skill. Another factor that makes things more difficult is that inside cannulas and catheters there are edges at widenings and connectors on which the tip of a microdialysis probe may catch and may possibly be bent, or damaged in some other way.

Another disadvantage is that the shape of the blood-filled space within a cannula or catheter becomes less regular when there is a microdialysis probe inserted or it may even happen that dead spaces are created in which the through-flow of blood is not optimum. In such cases, there is an increase in the tendency to become clogged and possibly in that for air bubbles to collect and, overall, in the falsification of the sensor signal and in the hazard to the patient.

SUMMARY OF THE INVENTION

It was therefore the object of the present invention to remedy the disadvantages described above by specifying a sampling device, a sampling system and a method of sampling and/or analysis. The sampling device, the sampling system and the methods should be as versatile as possible and should, as far as possible, be able to be used as part of clinical routine. The sampling device and the sampling system should be easy to sterilize and to keep sterile. The risks of clogging and of air bubbles collecting should be reduced. The sampling device and sampling system should be producible as inexpensively as possible. They should allow sampling to take place for a period of up to 8 days even without the individual sampling accesses being replaced and at the same time should in particular keep the width of fluctuations and the size of unavoidable sampling artifacts small when applied to human beings and in particular to the human circulation (e.g. in hemodialysis).

These and other objects are achieved in accordance with the invention by a sampling device, a sampling system, a method of sampling and a method of analysis as described below.

In accordance with the invention, there is therefore specified a sampling device for a sampling access, comprising
an analyte receiving chamber for receiving an analyte into a transporting medium, that is connected to an infeed-line passage and an outfeed-line passage for transporting the transporting medium respectively into and out of the analyte receiving chamber,
a sample chamber in the form of an internal cavity, having a sample inlet for receiving a sample that may possibly contain analyte, and
a separating medium surrounding the internal cavity, to allow the analyte to pass through from the sample chamber into the analyte receiving chamber.

The sampling device according to the invention is referred to a sampling access. A sampling access is a body that provides access to a medium intended for sampling. As a particular preference, the sampling device is referred to a medical sampling access and preferably to a hollow needle or cannula, a catheter, a port, an aspirator, a drain, a reservoir and/or a connector. The sampling device according to the invention is preferably and in particular adapted to pass through, to be inserted into, or to be fitted in some other way to, such a sampling access and in particular a medical sampling access and usefully a medical sampling access of the kind described. As a result of being so adapted, the sampling device according to the invention is advantageously arranged to come into contact with a medium intended for examination, and in particular with a body fluid of a human being and/or an animal, to allow a sample to be obtained. The sampling device according to the invention may equally well be adapted to a sampling access of a chemical reactor or bioreactor and in particular to a reactor connection such for example as a connection for sensors. For the design of such connectors and for the adaption for this purpose of a sampling device according to the invention those skilled in the art will for example consult Chmiel, Bioprozesstechnik, Einführung in die Bioverfahrenstechnik [Bio-process technology, Introduction to the technology of bio-processes], $1^{st}$ edition, 1999, chapters 8.11 and 8.12. The sampling device according to the invention can thus be used in a very versatile way.

The sampling device has a sampling chamber that takes the form of an internal cavity having a sample inlet to receive a sample that may possibly contain analyte. This internal cavity is surrounded by a separating medium, the separating medium enabling an analyte to pass through from the sample chamber into an adjoining analyte receiving chamber. Hence, in contrast to conventional microdialysis probes, the separating medium is not situated on the outside of the sampling device according to the invention but in the interior thereof. In an advantageously simple but at the same time reliable way, this enables any mechanical action on the separating medium other than by the sample intended for analysis to be largely or completely avoided. Advantageously, it is thus only very seldom and in exceptional cases that it happens that the separating medium is covered by a body other than the medium intended for sampling. Masking of parts of the separating medium such as may be caused by the wall of a blood vessel or even by the wall of a cannula or catheter when the separating medium is mounted on the outside of the sampling device is virtually ruled out with the sampling device according to the invention. In an advantageously simple way, this increases the repeatability and reliability of the sampling even when the sampling device according to the invention has been in place in a medium intended for sampling for a protracted period.

As a result of the provision of a separating medium permeable to analyte, it becomes possible in an advantageously simple way for the transporting medium to be kept free of a plurality of substances that may hamper a selected analyte from being determined in a sensor. The result is that the separating medium separates some of the analyte out of the sample and allows it to pass through into the analyte receiving chamber and the transporting medium situated therein. An enrichment of analyte in the transporting medium thus occurs in the analyte receiving chamber. The person skilled in the art will usefully select the size of the sampling chamber and the material, shape and thickness of the separating medium in the light of the given analyte and the given medium. In so doing, the person skilled in the art will be guided by the separating media, such as dialysis membranes and gas diffusion membranes, that are usual for the given analyte and for the given medium intended for sampling.

Preferred in accordance with the invention and also meant by the term "sampling device according to the invention" whenever used below is a sampling device according to the invention in which the analyte receiving chamber surrounds the sample chamber. The analyte receiving chamber thus forms as it were a ring in cross-section that encloses an inner circle, i.e. the sample chamber. By contrast, in the case of an analyte receiving chamber that is not arranged in accordance with the invention and that adjoins the sample chamber at only one point, analyte can only cross from the sample chamber into the analyte receiving chamber at this one point and not for example on the side of the sample chamber that is opposite from this point in cross-section. The analyte receiving chamber surrounding a sample chamber may thus also take the form in accordance with the invention of for example a channel surrounding the sample chamber, for example by allowing the channel to run round the sample chamber in a helix or a meander.

This produces a surface area through which an analyte can pass through from the sample chamber into the analyte receiving chamber that is advantageously large relative to the volume of the analyte receiving chamber. Compared with a sampling device whose analyte receiving chamber does not surround the sample chamber in the way described above, this makes possible an advantageously high rate of passage of the analyte into the transporting medium and in comparison with smaller areas the time required to enrich the transporting medium with a preselected amount of analyte can be reduced in an advantageous way, thus enabling the frequency of measurement to be increased and also improving the reliability of measurement by making it less likely that any particles present in the sample are able to block any significant part of the area against the passage of analyte.

Particularly preferred and also always meant except where otherwise noted is a sampling device according to the invention whose sample chamber takes the form of a passage extending through the sampling device. The sampling device thus has a sample inlet to the sample chamber and, at a further end of the passage forming the sample chamber, a sample outlet. The sample outlet enables the sample to be allowed to emerge through the sampling device into a space outside the sampling device. This makes it possible for example for the sampling device to be arranged in a loop at one end of which a sample is introduced from the main body of the medium and at the other end of which a sample that has passed through the sampling device is expelled back into the main body of the medium. Other advantageous embodiments of sampling devices and of sampling systems that are possible with a sampling device according to the invention having a sample chamber in the form of a passage will be described below particularly in the context of sampling systems, methods of sampling and methods of analysis according to the invention.

Those skilled in the art will appreciate that, where the sample chamber takes the form of a passage, the separating medium does not have to cover the entire length of the passage. It is enough simply for a sufficiently large portion of the separating medium to be present in the sample chamber so that the sample chamber and the analyte receiving chamber are separated from one another.

The sampling device according to the invention is preferably designed for fitting to a medical sampling access, and preferably a hollow needle and in particular a cannula, catheter, port, aspirator, drain, reservoir and/or connector. The sampling device is usefully designed in this case for connection to the sampling access, i.e. preferably to the medical sampling access, by positive interengagement and/or by a normal force and/or by friction. As a particular preference, the sampling device may be connectable by positive interengagement, by a normal force or by friction to a Luer lock connector, a bayonet joint and/or a screwed connector. Connectors and joints of this kind are widely used and standardized in medical engineering. The sampling device according to the invention can thus advantageously be fitted to and operated in a plurality of sampling accesses made by different manufacturers.

The sampling device is preferably designed to allow the analyte receiving chamber to be arranged
- within a main body of the medium intended for sampling, though a sampling access,
- in a sampling access,
- at an end of a sampling access that is remote from a main body of the medium intended for sampling, and/or
- in a line connected to a sampling access and outside a main body of the medium intended for sampling.

Hence, when samples are to be taken from a patient for example with the sampling device, meaning that his circulating blood for example forms the main body of the medium, then the sampling device may be designed to allow the analyte receiving chamber to be arranged
- in the interior of the patient, i.e. "upstream" of the sampling access, in a blood vessel,
- in a cannula, another hollow needle or a catheter,
- outside the patient, i.e. "downstream" of the sampling access, such for example in a Luer lock connector of a sampling access, and/or
- in a line connected to a sampling access, such for example as on a connector or a reservoir.

The same is true if it is not the circulating blood but some other part of a human or animal or some other medium from which a sample is to be taken.

Rather than being connectable to the sampling access by positive interengagement, by a normal force and/or by friction, and in particular rather than being designed for fitting to a medical sampling access, the sampling device according to the invention may also be integrally connected to the sampling access. The sampling device may then in particular be so arranged in a medical sampling access, and in particular in a cannula or another hollow needle, catheter, port, aspirator, drain, reservoir and/or connector, that, when the sampling access is used as intended, the sampling device is arranged either in the interior of the patient, i.e. at the tip of the sampling access for example, or in the sampling access, or "downstream" of the sampling access, i.e. outside of the patient. It is a particular preference in this case for the sampling device to be an integral part of a hollow needle and in particular of a cannula and/or of a catheter. By the placing of a sampling device of this kind according to the invention, it is possible in one step both for a sampling access to be created and for the sampling device itself to be arranged in the patient, without there being any concern when this is done that all or part of a solid body in the patient, such for example as of the wall of a vessel, may rest against the separating medium and thus hamper an analyte from crossing from a sample into the analyte receiving chamber.

The sampling device according to the invention, be it integrally connected to a sampling access or, as is preferred, being able to be fitted thereto, is preferably designed to receive a sample of body fluid, the body fluid preferably being selected from blood, blood plasma, lymph, tissue fluid, cerebrospinal fluid, synovial fluid, gastric juice, gall and urine. However, the sampling device according to the invention is not limited to such samples and in other preferred embodiments is designed to receive a sample of a cell culture, preferably a liquid cell culture, and/or of the liquid and/or gaseous content of a biological or chemical reactor. The person skilled in the art will obviously select the size of the sampling chamber for example to suit the sample to be examined and, if necessary, also as a function of the sampling location selected in the given case.

For the purposes of the present invention, a sensor is any device or group of devices that generates a measurement signal as a function of the presence or quantity of an analyte. A sensor may in particular be selected from the group comprising electrochemical sensors, optical sensors, amperometric sensors, conductivity sensors, potentiometric sensors, biosensors, oxygen sensors, enzymatic sensors, spectral photometers, NIR analyzers, IR analyzers, fluorescence photometers and sample sensors for gas chromatographs or HPLC apparatus.

The person skilled in the art will select the separating medium to suit the intended purpose. What are preferred in accordance with the invention are sampling devices in which the separating medium is a membrane, preferably a dialysis membrane. Hence, where there is mention of a separating medium in the present description, what is always also, i.e. in addition, meant is an embodiment whose separating medium is a membrane and preferably a dialysis membrane. For the purposes of the invention, dialysis membranes are membranes that allow chemical compounds to pass through them only when the compounds are up to a certain size. Dialysis membranes for example allow ions such for example as $Na^+$ to be separated from other charged or uncharged substances of a larger size such for example as peptides or proteins. In the light of the given analyte and, if required, of the given sensor too, the person skilled in the art will be able to select a suitable membrane, and in particular a suitable dialysis membrane.

When the separating medium is a membrane (also referred to below as a "sample membrane"), then the material of the sampling membrane is preferably selected from the group comprising cellulose and derivatives thereof and in particular cellulose acetate, PTFE, polycarbonate, polypropylene, polyamides, polyesters, polyethersulfones and polysulfones.

Also preferred is a sampling device according to the invention whose separating medium, and in particular whose sample membrane, is designed to allow to pass through it an analyte selected from glucose, lactose, lactate, $Na^+$, $K^+$, $Cl^-$, $H_3O^+$, $O_2$, $CO_2$, ammonium, ammonia, methanol, ethanol, formate, acetate, glutamine, glutamate, urea, uric acid, phosphate, antibodies, growth factors, hormones, medications, and in particular narcotics and anesthetics.

The inside diameter of the infeed-line passage and/or the outfeed-line passage of a sampling device according to the invention, at the analyte receiving chamber or at the narrowest point of the passage in the sampling device, is from 0.01 to 2 mm, preferably 0.1 to 1.5 mm, and as a particular preference 0.25 to 0.5 mm. With inside diameters of this kind, it is possible to generate such high pressures, even when aqueous transporting media are used in clinical applications, that fast flow of the transporting medium, substantially in plug form, can be obtained from the analyte receiving chamber towards and into a sensor, without the possibility of the lines used to convey the transporting medium pulling loose from the sampling device or of the separating medium, in particular the sample membrane and in particular a dialysis membrane, splitting having to be a cause for concern.

As an alternative to such dimensions for the inside diameter or as an addition thereto, it is preferred for the area of that portion of the separating medium that connects the sample chamber to the analyte receiving chamber (hereinafter referred to as the "membrane window") to be 0.5 to 350 $mm^2$, preferably 1 to 50 $mm^2$, and as a particular preference 2 to 35 $mm^2$. These sizes for the membrane window are adapted in a particularly advantageous way to the dimensions that exist in catheters and cannulas and they do allow analyte to pass through quickly due to the surprisingly large area of the membrane window. What proved particularly successful in initial trials was an area of 34 $mm^2$ for the membrane window. The diameter of the outfeed-line passage, which was circular in cross-section, was 0.23-0.26 mm, preferably 0.25 mm, in this case.

In a preferred embodiment, the ratio of the area of membrane window to the minimum cross-sectional area of the outfeed-line passage is not more than 400:1, preferably not more than 200:1, and as a particular preference 40:1 to 80:1. In another embodiment, the ratio is preferably more than 400:1, preferably 450:1 to 1000:1, and as a particular preference 500:1 to 750:1.

The sampling device according to the invention preferably further comprises a movable closing-off membrane for reducing and/or closing off a volume of the sample chamber or the sampling access. In this case the sampling device usefully further comprises a passage for controlling the closing-off for exerting a pressure to move the closing-off membrane. In an advantageously simple way, it becomes possible by means of the closing-off membrane for the sample chamber to be divided off from the main body of the medium intended for sampling by filling a volume of space that is situated upstream of the analyte receiving chamber (i.e. upstream of the membrane window) in the direction of flow of the medium. It can be ensured in this way that there is a stationary sample in the sample chamber, or the dead volume in the sampling access, can be reduced. However, the closing-off membrane may also, alternatively or in addition, be so designed that it is able to open or reduce a volume of the sample chamber at a point downstream of the analyte receiving chamber (i.e. downstream of the membrane window) in the direction of flow of the medium. This makes it possible for a sample to be drawn into the sample chamber by suction or expelled from the sample chamber.

When a multilumen catheter is used, the sampling access may for example be so designed that the lumen connected to the sampling device can be reversibly closed off by inflation by means of a membrane tube inserted into the interior of the lumen. In this way, the dead volume can be reduced between the samplings of the medium and it can be ensured that the sampling infeed is sealed off reliably. Similar arrangements are also conceivable for cannulas or other sampling accesses.

Also preferred is a sampling device according to the invention that comprises an alternative outlet to allow medium held in the sample chamber to leave. A sampling device of this kind has a sample chamber in passage form that has three exits, namely the inlet for the sample, the other outlet of the passage that is described above, and the above-mentioned alternative outlet. Particularly in conjunction with a closing-off membrane, it is then possible for a sample to be allowed to leave the sampling device via the outlet of the passage and/or the alternative outlet. A particularly simple option for calibration with the help of a sampling device according to the invention becomes possible in this way: for this purpose, in a first step, any sample material present in the sample chamber is driven out by applying a calibrating medium to the sample chamber. If the sampling device has a closing-off membrane, this is usefully closed off to prevent medium intended for sampling from entering the sample chamber. The sample that may be present in the sample chamber is then driven out of the sampling device according to the invention by the calibrating medium through the alternative outlet. If the sampling device does not have a closing-off membrane, it is useful for a pressure lower than the pressure of the calibrating medium and the pressure of the medium intended for sampling to be applied to the alternative outlet, what thus leaves the alternative outlet being a mixture of calibrating medium and the medium intended for sampling. If the alternative outlet is arranged between the sample inlet and the analyte receiving chamber (i.e. the membrane window), then this ensures on the one hand that no calibrating medium is forced into the medium intended for sampling (the main body of the medium) (because the medium intended for sampling is still being drawn out by suction through the alternative outlet in the present case) but on the other hand that no medium intended for sampling finds its way to the membrane window (the calibrating medium is in fact flowing in from this direction).

Also specified in accordance with the invention is a sampling system comprising
 a sampling device,
 a sensor connection for connecting in a sensor for detecting an analyte in a transporting medium,
 an infeed line, in fluid communication with the infeed-line passage in the sampling device,
 an outfeed line, in fluid communication with the outfeed-line passage in the sampling device and with the sensor connection,
 a first pump to transport a medium through the outfeed line to the sensor connection.

Except where otherwise stated, the sampling device is a sampling device according to the invention as described above. Alternatively, it is also possible for use to be made in a sampling system according to the invention of a sampling device whose analyte receiving chamber does not surround an internal sample chamber but is connected to the medium intended for sampling by a membrane window arranged on the outer edge of the sampling device. A sampling device of this kind is preferably arranged in a hollow needle and preferably a cannula or catheter.

A sampling system according to the invention provides the advantages that can be obtained with the sampling device according to the invention. In particular, the sampling system according to the invention allows transporting medium, possibly charged with analyte, to be transported from the analyte receiving chamber of the sampling device to a sensor connection and, if a sensor is connected in, even into the sensor to allow the transporting medium to be examined.

The first pump of the sampling system according to the invention may in particular be arranged in the infeed line or upstream thereof in the direction of transport of the medium. When this is the case the pump generates a pressure to force the transporting medium through the infeed line, the analyte receiving chamber and the outfeed line to the sensor connection. The pump, may however also be arranged between the outfeed-line passage of the sampling device and the sensor connection, preferably in the outfeed line. When so arranged between the outfeed-line passage of the sampling device and the sensor connection, the first pump generates a pressure below atmospheric on one side, to draw transporting medium through the infeed line and into the analyte receiving chamber of the sampling device and out thereof, whereas on the other side it generates a pressure above atmospheric to transport the transporting medium through the outfeed line to the sensor connection and possibly into a sensor. In a third embodiment, the first pump may be connected downstream of the sensor connection, and in particular downstream of a sensor, in the direction of transport. When this is the case, the pump, as it operates, generates a pressure below atmospheric to draw transporting medium by suction through the infeed line, the analyte receiving chamber and the outfeed line to the sensor connection and preferably through the sensor.

The arrangement of the first pump in or upstream of the infeed line is a particular preference in cases where it is important for the transporting medium to be transported quickly. By applying a small pressure above atmospheric, what is achieved is that all the lines required for the transport and also the separating medium, and in particular the separating membrane of the sample chamber, are expanded when seen from the transporting medium, and it is thus not possible for the lines to collapse as they might if there were a pressure below atmospheric.

In cases where the prevention of contamination of the medium intended for sampling is a very high priority, it is preferred for the first pump to be arranged between the outfeed-line passage and the sensor connection or, in the direction of movement of the medium, downstream of the sensor connection and possibly of the sensor. This is also an advantageously easy way of preventing transporting medium from getting into the medium intended for sampling even if the separating medium and in particular a separating membrane is damaged, in that, in the analyte receiving chamber, a pressure below atmospheric relative to the medium intended for sampling is applied as the transporting medium is transported. This being the case, it is only transporting medium that is drawn by suction through and out of the analyte receiving chamber. If the separating medium were damaged, transporting medium and medium intended for sampling would be drawn out of the analyte receiving chamber.

A sampling system that is preferred in accordance with the invention further comprises a sampling line and, connected thereto, a second pump for pumping a sample into the sample chamber. Except where otherwise stated, it is always also a sampling system of this kind that is meant in the remainder of the description of the present invention. Further descriptions of the sampling system according to the invention thus relate both to a sampling system not having a second pump and to a sampling system having a second pump. If the sampling device of the sampling system according to the invention is not a sampling device according to the invention but is arranged in the interior of a hollow needle, then the sampling line is connected to the hollow needle to allow a sample to be pumped into the inner lumen of the hollow needle that acts as a sample chamber.

Known from WO 2008/059050 A2 is an indwelling venous catheter having an analyte delivery chamber, the analyte delivery chamber being connected to an internal cavity in the cannula to allow a medium present in the cavity to be sampled. However, this document does not teach the surrounding of the sample chamber with a separating medium to allow the analyte to pass through into the analyte delivery chamber not does it teach the drawing of a medium into the internal cavity by suction. It also fails to teach the control of a pump device as a function of this drawing-in by suction (a subject that will be dealt with shortly) to allow a sample of a transporting medium that may possibly contain analyte to be obtained. Nor does the document give any indication that this indwelling venous catheter can be developed to achieve the above-mentioned objects of the invention. Instead, there is only an incidental mention of the individual indwelling venous catheter as such.

The second pump advantageously allows a sample of a medium intended for sampling to be drawn into the sample chamber by suction. A person skilled in the art will appreciate that the purpose of this drawing-in by suction is to cause an analyte from the sample to enter the analyte receiving chamber of the sampling device through the separating medium, and in particular through a separating membrane, in order to charge the transporting medium present in the analyte receiving chamber with the analyte. The person skilled in the art will easily be able to select the quantity of medium to be fed in, and hence the size of the sample, as a function of the volume of the sample chamber and the arrangement of the analyte receiving chamber, to deal with his particular measurement problem. A particular preference is for the sample chamber of the sampling device to be completely filled with the medium intended for sampling.

It is also possible and preferred for more medium to be drawn in by suction through the sampling line, by means of the pump, than the sampling device is able to hold in its sample chamber. Some medium intended for sampling then escapes into the sampling line. It is possible in this way for the sample chamber to be completely flushed out with the medium intended for sampling. In particular, such a procedure prevents the medium drawn into the sample chamber by suction from being only that which is spaced between the main body of the medium and the membrane-window in the form of a dead volume. If for example the sampling device is arranged in a hollow needle, and in particular in a catheter or cannula, it might happen if the sampling volume were too small that the medium that made its way into the sample chamber was only that which was situated in the tip of the hollow needle, upstream of the sample chamber in the direction of drawing in, and thus not in the actual flow of medium. A volume of medium of this kind may be of a different composition than the medium forming the main body of the medium because unmixing and clotting processes for example may occur in a volume of medium that is largely stationary. However, by drawing a volume of medium that is selected to be sufficiently large into the sample chamber and the sampling line, it is possible to avoid sampling only such dead volumes of medium. To avoid such dead volumes, it is also useful for use to be made in addition of a movable closing-off membrane as described above. Surprisingly, however, measurements can be made from a mixture of a sample and a dead volume of medium, even repeatably.

A sampling system according to the invention, i.e. a sampling system having a first and preferably also a second pump as described above, preferably further comprises a supply of transporting medium and/or a supply of calibrating medium and/or a supply of flushing medium. The particular supply of medium or the two supplies of medium or all the supplies of medium are in fluid communication with the infeed line or can be put into such communication. If the sampling system also comprises a sampling line, it is preferred for one, two or all the supplies of medium to be in fluid communication with the sampling line or to be able to be put into such communication.

For the purposes of the present invention, a transporting medium is a preferably liquid and in particular preferably aqueous, but possibly even gaseous, medium that is suitable for transporting the analyte intended for determination to a selected sensor. A person skilled in the art can easily select a suitable transporting medium in the light of the analyte intended for determination, the medium intended for sampling, the sensor and the operating parameters of the sampling system according to the invention, such for example as the temperature, or the diameters of the lines used. If the medium intended for sampling is a body fluid, and in particular blood, blood plasma, lymph, tissue fluid or cerebrospinal fluid, it is preferred for the transporting medium to be an isotonic saline solution, a particular preference being a solution of 0.9% by weight of NaCl in water. Also preferred are balanced electrolyte solutions of physiological osmolarity. Transporting media that are adapted to the physiological osmolarity, and in particular have an osmolarity that is almost or completely identical to the physiological osmolarity, enable samples to be taken of a body fluid, and in particular of the body fluids mentioned, without the passage through the separating medium, and in particular the separating membrane, of the analyte being falsified by the simultaneous passage through of an excessive amount of water.

The transporting medium may contain other substances, in particular as a function of the analyte intended for determination and the sensor used for this purpose. The transporting medium may for example contain reagents that react with the analyte intended for detection, the result of the reaction being determined in the sensor. Examples of such other substances are dyes and in particular fluorescent dyes.

For the purposes of the present invention, a calibrating medium is a medium that contains a concentration of one or more analytes intended for determination that is known beforehand. The main purpose of the calibrating medium is then to calibrate a sensor to this concentration or these concentrations. For this purpose, the calibrating medium may be fed to a sensor by (a) introducing the calibrating medium into the sample chamber to charge the transporting medium with the analyte and then transporting the charged transporting medium to the sensor outlet and preferably to the sensor, (b) flushing calibrating medium through the analyte receiving chamber and transporting the calibrating medium to the sensor outlet and preferably to the sensor, and/or (c) applying the calibrating medium directly to the sensor or sensor outlet, i.e. by bypassing the sampling device.

For the purposes of the present invention, a flushing medium is a medium that is arranged for the flushing through of the sample chamber and/or the analyte receiving chamber, preferably to clean them of calibrating medium and/or transporting medium, in particular transporting medium containing analyte. The flushing medium and the calibrating medium too are preferably of the same or approximately the same osmolarity as the transporting medium. If the flushing medium and/or the calibrating medium is introduced into the sample chamber, thus enabling it to make its way from there into a patient (human or animal), it is preferred for a physiologically compatible medium to be used as the calibrating medium and/or the flushing medium, i.e. preferably an isotonic saline solution or a transporting medium as described above.

Also a particular preference in accordance with the invention is a sampling system in which the first pump is arranged between (a) the supply of transporting medium and/or the supply of calibrating medium and/or the supply of flushing medium and (b) the infeed-line passage of the sampling device, to allow medium to be transported from the given supply of medium through the infeed line and into the infeed-line passage. Advantages provided by the arrangement of the first pump in this way have already been described above.

A sampling system according to the invention preferably further comprises a bypass line for the fluid communication of the supply of transporting medium and/or the supply of calibrating medium and/or the supply of flushing medium with the sensor connection, without the medium passing through the analyte receiving chamber of the sensor device. In an arrangement of this kind it is advantageously possible for analyte-free transporting medium, flushing medium and/or calibrating medium to be conveyed directly to the sensor outlet and, if a sensor is present, to the sensor itself, for example to flush out or calibrate the sensor. Should the calibrating medium and/or the flushing medium be physiologically incompatible, this arrangement also provides the advantage of keeping the calibrating medium and/or the flushing medium away from the sampling device as far as is possible, which means that even should the separating medium, in particular the separating membrane, be damaged, any contamination of the sample or of the main body of the medium with the calibrating medium and/or the flushing medium can be ruled out.

It is also preferred for the bypass line to be connected to the outfeed line by a switchable connection. A switchable connection of this kind provides an additional measure of security against inadvertent mixing of transporting medium, possibly containing analyte, that is transported through the outfeed line with transporting medium, calibrating medium and/or flushing medium still present in the bypass line.

Also preferred is a sampling system according to the invention that comprises a switchable connection for the alternative placing in fluid communication of the supply of transporting medium and/or the supply of calibrating medium and/or the supply of flushing medium with either the infeed line or the bypass line. A switchable connection of this kind may be provided in addition or as an alternative to a switchable connection for connecting the bypass line to the outfeed line. The switchable connection for place the given supply of medium in communication with the infeed line or bypass line makes it possible, in an advantageously easy way, for contamination of the transporting medium, the calibrating medium and/or the flushing medium with any calibrating medium, flushing medium and/or transporting medium that may be present in the bypass line or infeed line to be prevented. In this way, it can for example be ensured that calibrating medium always flows only into the bypass line, whereas transporting medium and flushing medium can be conveyed through the infeed line without coming into contact with the calibrating medium.

A sampling system according to the invention is also preferred when it comprises an outflow line for putting the outfeed line into fluid communication with the sampling line, via the sensor connection and possibly via a sensor. It becomes possible in this way for medium that has been examined by the sensor, rather than being taken to a container for waste medium, to be fed into the medium intended for sampling through the sampling line and to be disposed of in this way if required. If the medium sampled intended for sampling is a medium from a human or animal patient, and in particular a body fluid, it is useful for the sampling system according to the invention to be of sterile nature. This applies particularly when, as just described, an outflow line is provided for putting the outfeed line into fluid communication with the sampling line via the sensor connection and possible via a sensor.

What is particularly preferred in this case is a sampling system that comprises a switchable connection for the alternative putting into fluid communication (a) of the outfeed line with the outflow line, possibly via a sensor, or (b) of the outfeed line with a waste line, possibly via a sensor, to convey medium emerging from the outfeed line, possibly through the sensor, to a means of disposing of medium. In this way, it can be selected whether a medium emerging through the sensor connection and possibly through the sensor is to be disposed of or is to be fed into the medium intended for sampling.

If, as is preferred, a sampling system according to the invention comprises a sampling line and a second pump, a particular preference is for the sampling system to comprise in addition a switchable connection for connecting the supply of transporting medium and/or the supply of calibrating medium and/or the supply of flushing medium to the sampling line via the second pump. This makes it possible for a transporting medium, a calibrating medium and/or a flushing medium to be applied to the sample chamber of the sampling device. A particular preference is for calibrating medium and/or flushing medium to be able to be applied to the sample chamber in the way described. When calibrating medium is applied to the sample chamber, it is possible, as described above, for a transporting medium in the analyte receiving chamber to be charged with an analyte from the calibrating medium to allow appropriately charged transporting medium to be transported through the outfeed line to the sensor connection and usefully to the sensor. The signal from the analyte that is measured at the sensor can then be correlated with a known concentration of analyte in the calibrating medium. In this way, a very precise conclusion can be drawn about the actual concentration of analyte in the medium being sampled because possible sources of measurement errors such as result from the crossing that the analyte necessarily has to make from the calibrating medium, through the separating medium and in particular a separating membrane, and into the analyte receiving chamber can be ruled out or appreciably reduced. A particular preference is then for a sampling system according to the invention to comprise a sampling device having an alternative outlet, the alternative outlet being arranged, as a particular preference, downstream of the membrane window in the direction of flow of the calibrating medium and/or the transporting medium and/or the flushing medium. This makes it possible, as described above, for the sample chamber to be flushed with calibrating medium and/or flushing medium and/or transporting medium and for the medium used for the flushing to be allowed to leave through the alternative outlet rather than exiting into the supply of the medium intended for sampling. It is also preferred in this case, as was also described above, for a sampling device to be used that has a closing-off membrane, or for the leaving of a medium through the alternative outlet to be controlled by a further pump.

The sampling system according to the invention preferably has a control system, connected to the second pump, to control the second pump in such a way that Step 1: a sample is drawn by suction into the sample chamber, Step 2: the sample that was drawn in is present in the sample chamber for a preselected time and then Step 3: the sample that was drawn in is expelled from the sample chamber.

In a surprisingly simple and advantageous way, a sampling system that is controlled in this way allows repeatable analyte concentrations to be obtained in the sample that possibly contains analyte, this concentration being in a calibratable relationship with the analyte concentration in the medium intended for examination. A particularly advantageous effect is that, when the sampling system is applied to a living entity, in particular to a human being, the sampling device can remain inserted in the living entity for a protracted period, the effect of involuntary movements or fluctuations in blood flow being reduced in comparison with a microdialysis probe implanted in the conventional way. A further advantage is that a sampling system as described above may have the sampling line in the formed of a loop, which means that after passing through the sampling device and the possible crossing of the analyte into the transporting medium, a sample taken from the main body of the medium can be fed back into the latter. If for example the sampling device is connected to a patient's blood stream, this arrangement allows blood to be taken without any substantial loss of blood to the patient.

If as described above the sampling system according to the invention comprises a hollow needle, i.e. if a sampling device according to the invention is connected into or onto a hollow needle or a sampling device that is not according to the invention is inserted into a hollow needle, then the hollow needle is preferably a cannula, an indwelling cannula, a catheter or an indwelling catheter. Such devices are known particularly from the medical field; they are produced in large numbers with repeatable characteristics and are considered safe for use on a human being. As a particular preference, the inside diameter of the hollow needle is from 0.8 to 1.3 mm. What can be achieved in this case by a suitable arrangement of the analyte receiving chamber in the hollow needle is that a sample of the medium intended for analysis of 50 to 150 µl is enough to cover the separating medium, and in particular a separating membrane, at the membrane window reliably, a sample volume of 75 µl being preferred when the inside diameter of the hollow needle is 0.96 mm and the distance from the closest edge of the membrane window to the tip of the hollow needle is 3 mm. Similarly preferred are sample volumes that are increased or reduced in proportion as the inside diameter of the hollow needle and/or the distance between the edge of the membrane window and the tip of the hollow needle are/is increased or reduced. Particularly when the sampling device according to the invention is applied to a patient, the stress on the patient due to the sampling can be kept low in this way. If the cross-section of the hollow needle is other than circular, being for example oval or rectangular, then it is preferable for the details given above to be adapted to the given hollow needle in such a way that in each case the cross-sectional area corresponds to the area of a circular cross-section of the diameters given above. The inside diameter of the outfeed line and the infeed line and also of the outfeed-line passage and the infeed-line passage is preferably 0.15 to 0.8 mm, the diameters that are given in WO 2008/059050 being a particular preference.

If as described above the sampling system comprises a hollow needle, then it is preferable for the sampling device according to the invention to be supplied in a form where it is, integrally connected to the hollow needle. At a preselected point, the hollow needle then contains a membrane window and an analyte receiving chamber that preferably surrounds the sample chamber. In an advantageously simple way, a design of this kind avoids the problem of a sampling device having to be inserted into the interior of a hollow needle separately and in particular against a flow of blood.

As an alternative to this, the sampling device may also be detachably connected to the hollow needle as described above. This design is advantageous and preferred particularly when the sampling access to the medium intended for sampling is to remain in place for a period longer than that for which the sampling device is to remain in contact with the medium intended for sampling. It may for example be advantageous for a cannula to be placed in a patient for a period of 4 weeks but for the sampling device to be changed every week.

A sampling system according to the invention preferably comprises a control system that is connected to the first pump, to control the latter pump in such a way that, in step 2:

Step a): transporting medium is present in the analyte receiving chamber for a preselected time and then Step b): transporting medium possibly containing analyte is transported from the analyte receiving chamber into the outfeed-line passage. A control system of this kind thus matches the operation of the first and second pumps to one another to allow an analyte to pass through from a sample into the transporting medium and to allow the transporting medium, that may possibly be charged with analyte, to be transported out of the analyte receiving chamber. For the transport, the analyte receiving chamber can be flushed with transporting medium, flushing medium or calibrating medium as described above.

The control system is preferably also arranged to control the first pump in such a way that Step c): after step b) transporting medium possibly containing analyte is transported from the outfeed-line passage to the sensor connection.

This transport may, but does not have to, take place in step 2. Once again, the analyte receiving chamber may be flushed with transporting medium, flushing medium or calibrating medium in step c) as described above. If a sensor is connected to the sensor connection, then the control system is usefully so arranged that transporting medium possibly containing analyte is transported into the sensor.

Fitted in fluid communication to the sensor connection of a sampling system according to the invention is preferably a sensor that is arranged to determine an analyte selected from glucose, lactose, lactate, $Na^+$, $K^+$, $Cl^-$, $H_3O^+$, $O_2$, $CO_2$, ammonium, ammonia, methanol, ethanol, formate, acetate, glutamine, glutamate, urea, uric acid, phosphate, antibodies, growth factors, hormones, medications, and/or narcotics and anesthetics.

A method of sampling according to the invention comprises the following steps:

1) drawing of a sample by suction into a sample chamber of a sampling device according to the invention, 2) making available of a transporting medium in the analyte receiving chamber for a preselected time to allow an analyte possibly contained in the sample to enter the analyte receiving chamber, 3) expulsion of the sample that was drawn into the sample chamber, and 4) before, simultaneously with, or after step 3), transport of the transporting medium out of the analyte receiving chamber. A method of analysis according to the invention corresponds to the method of sampling according to the invention, with the transporting medium possibly charged with analyte being conveyed, in step 4), out of the analyte receiving chamber to a sensor for determining the analyte. The method of sampling according to the invention and the method of analysis according to the invention give the advantages that are described above for the invention.

Preferably in a further step, the analyte receiving chamber and/or the sensor are/is flushed with analyte-free transporting medium, flushing medium or calibrating medium. Suitably arranged sampling devices and sampling systems according to the invention are described above.

What is therefore preferred is a method of sampling or method of analysis according to the invention that further comprises the step of applying a calibrating medium to the analyte receiving chamber by feeding the calibrating medium into the analyte receiving chamber through the infeed-line passage.

Also preferred is a method of sampling or analysis according to the invention that comprises the step of:

producing a calibrated concentration of an analyte in the analyte receiving chamber by 1. feeding the calibrating medium into the sample chamber and 2. allowing analyte to pass through from the sample chamber into a transporting medium in the analyte receiving chamber for a preselected period of time.

If a calibrating medium is used in a method of sampling and/or analysis according to the invention, then it is preferred for the reasons stated above in connection with the sampling device according to the invention and the sampling system according to the invention for the calibrating medium to be allowed to leave through an alternative outlet belonging to the sampling device.

The invention will be described in detail below by reference to the drawings and to selected embodiments, although this description does not limit the scope of protection of the claims.

BRIEF DESCRIPTION OF THE DRAWINGS

In the drawings:

FIG. 6a is a schematic view of the exterior of a sampling device that is designed in the form of a probe.

FIG. 6b is a schematic view of the use of sampling devices in conjunction with a sampling access in the form of a catheter.

FIGS. 7a and 7b are schematic views of the use of a, sampling device according to the invention in conjunction with a sampling access in the form of a cannula.

DETAILED DESCRIPTION OF THE INVENTION

Figure 1:
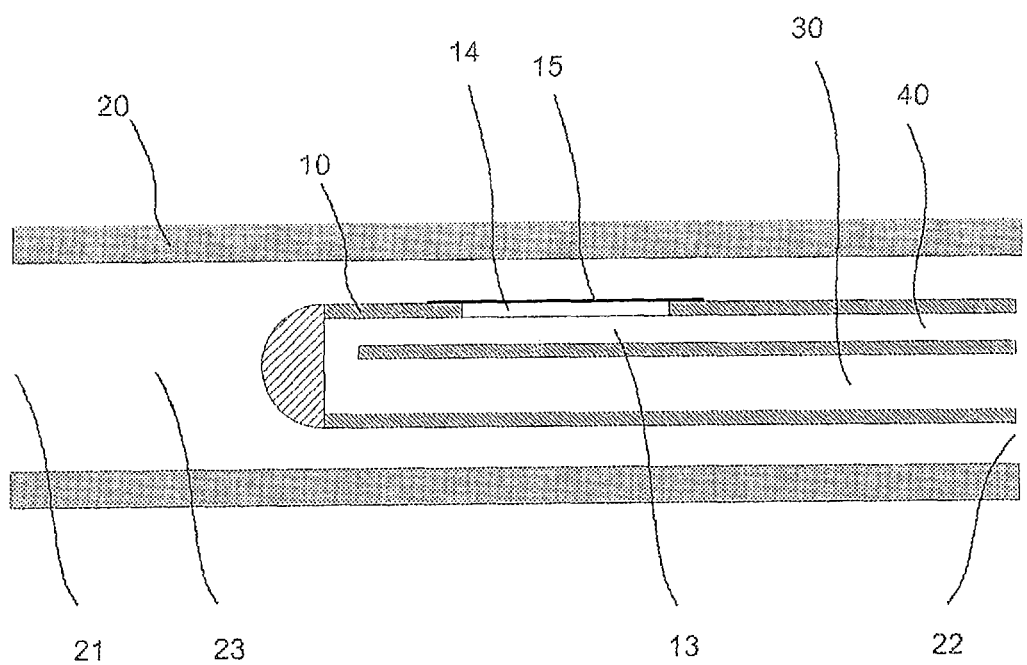
FIG. 1 is a schematic view in cross-section of a sampling device comprising a window provided with a separating medium, by which the sample chamber and the analyte receiving chamber are connected together.

FIG. 1 shows a sampling device 10 having a hollow needle 20. The hollow needle 20 forms a tube of circular cross-section that constitutes the sample chamber 23. The sample chamber 23 has two openings, with the first opening of the sample inlet being 21 and possibly being pointed (not shown) to make it easier for the hollow needle 20 to be inserted into a patient. The second opening 22 is connected by a sampling line (not shown) to a second pump 90 (not shown) to allow a flushing medium to be driven through the sample chamber 23 from the sample inlet 21 to flush the sample chamber 23 or to allow a medium intended for sampling to be drawn by suction into the interior of the sample chamber 23 through the sample inlet 21.

The sampling device 10 has an internal cavity 13. The internal cavity 13 is in fluid communication with an infeed-line passage 30 and outfeed-line passage 40 arranged in the interior of the sampling device 10. In the region of the internal cavity 13, the outer wall of the sampling device 10 is pierced in the form of a window and the window 14 is closed off by a separating membrane 15. From the sample chamber 23, an analyte is able to diffuse through the separating membrane 15 into the internal cavity 13 and the internal cavity 13 forms an analyte receiving chamber.

In operation, the sampling device 10 is first inserted into a patient or a sampling access, such for example as a hollow needle 20, in particular a cannula or catheter or the sampling access of a bioreactor. If the hollow needle 20 is an 18 gauge hollow needle, the distance between the sample inlet 21 and the tip of the sampling device 10 is preferably approximately 3 mm. The sample chamber 23 is then flushed with a flushing medium. At the same time or following this, the analyte receiving chamber 13 is flushed with transporting medium.

A sample of a medium intended for sampling, such as blood for example, is then drawn by suction into the sample chamber 23 that has been flushed, the separating member 15 thus being completely or, to a preselected degree, incompletely covered by the sample in the region of the window 14 of the analyte receiving chamber 10. If the hollow needle 20 is an 18 gauge hollow needle, 75 µl is preferably enough for this.

After the drawing in of the sample, a wait is made for a preselected time to give the analyte or analytes an opportunity to diffuse into the analyte receiving chamber 13. As an alternative to this, sample material may also be drawn by suction into the sample chamber 23 for a preselected time and, as a option, it may flushed out, to ensure that there is as constantly high as possible a concentration of analyte in the interior of the sample chamber 23, thus enabling as high a concentration of analyte as possible to be obtained in the analyte receiving chamber 13.

Then or at the same time, transporting medium is flushed through the infeed-line passage 30 to transport the volume of transporting medium out of the analyte receiving chamber 13 and through the outfeed-line passage 40 to a sensor (not shown). The sensor is arranged for the qualitative and/or quantitative detection of the analyte. As the analyte receiving chamber 13 is flushed, the interior of the sample chamber 23 too is usefully flushed with a flushing medium to drive the sample out of the sample chamber 23 and limit any further entry of the analyte into the analyte receiving chamber 13.

Figure 2:
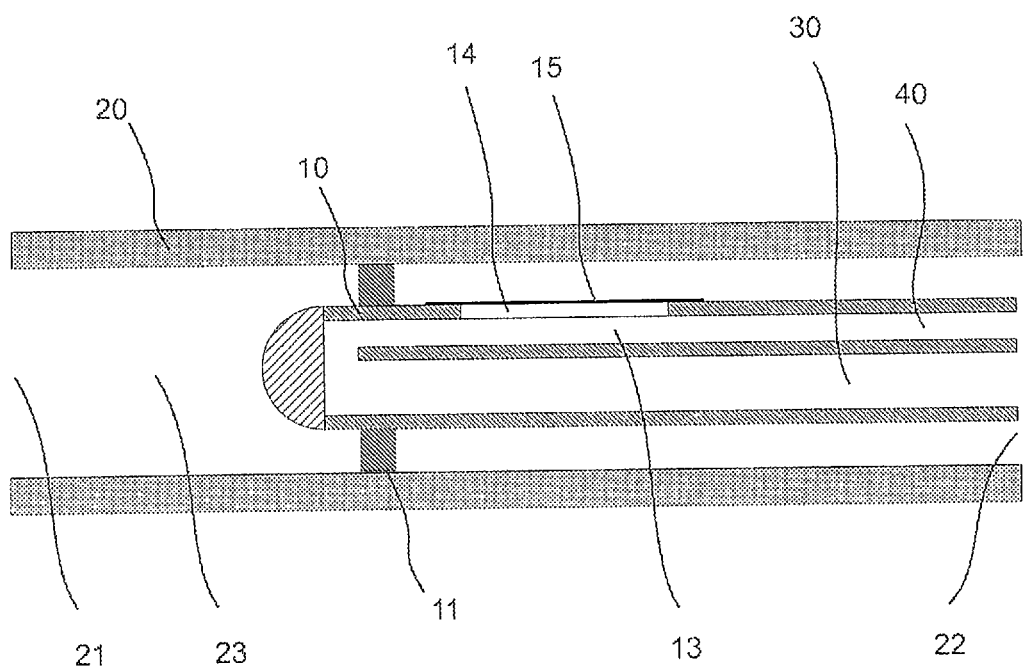
FIG. 2 is a schematic view in cross-section of a sampling device as shown in FIG. 1 having spacers.

FIG. 2 differs from FIG. 1 only in that a spacer 11 is provided in this case to keep the sampling device 10 spaced away from the inner walls of the hollow needle 20. It is ensured in this way that the separating membrane 15 remains free in the region of the window 14 of the sampling device 10 for the analyte to pass through and is not accidentally wholly or partly closed off by the inner wall of the hollow needle 20.

Figure 3:
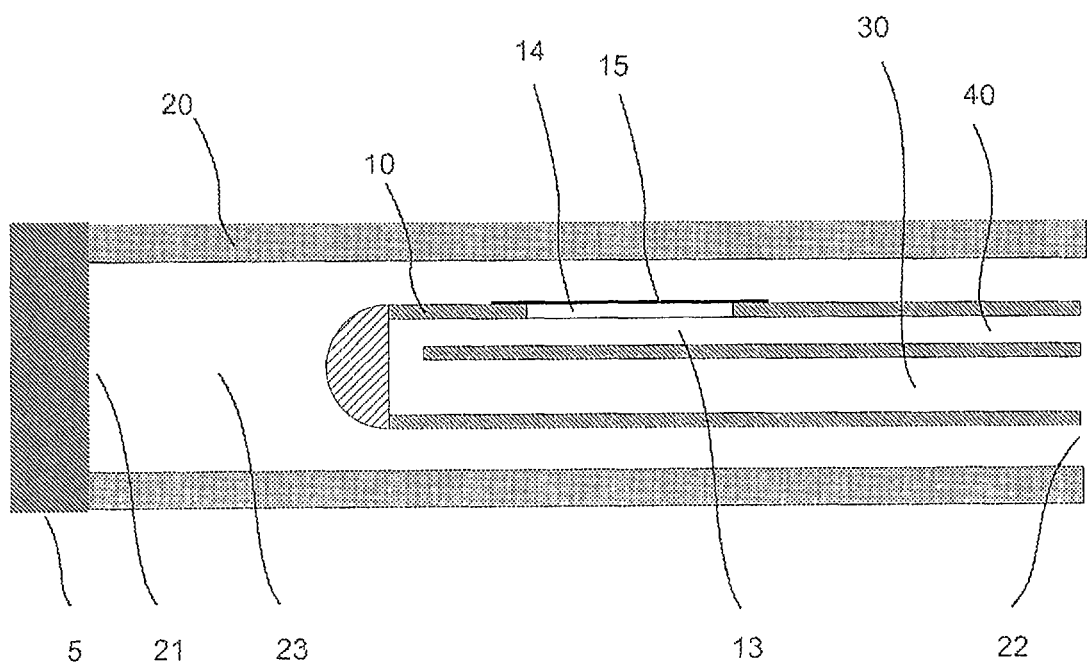
FIG. 3 is a schematic view in cross-section of a sampling device as shown in FIG. 1 having a filter.

FIG. 3 differs from FIG. 1 only in that a filter 5, preferably a sterile filter, is mounted at the sample inlet 21. Microorganisms can be prevented from entering the interior of the hollow needle 20 in this way. Deposits or biofilms can thereby be prevented from forming in the interior of the hollow needle 20. It is also possible to in this way stop the medium intended for sampling from being contaminated by the flushing medium. This is particularly for use on bioreactors, where cells are to be prevented from making their way into or out of the medium intended for sampling.

Figure 4:
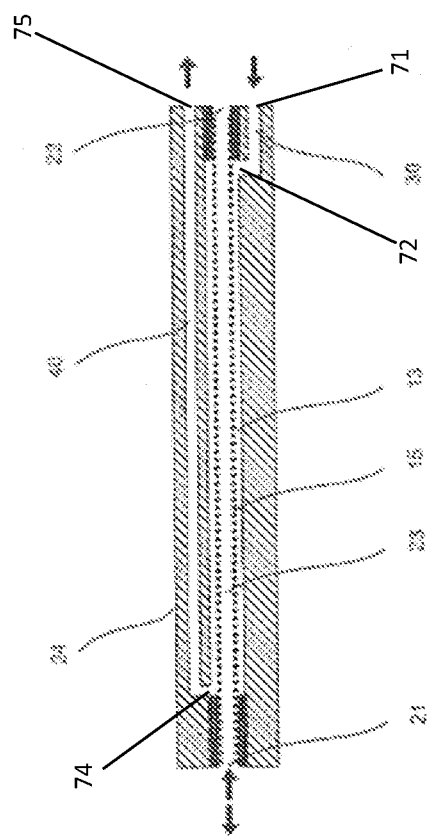
FIG. 4 is a schematic view in cross-section of a sampling device according to the invention, with the analyte receiving chamber surrounding the sample chamber and the sample chamber taking the form of a passage extending through the sampling device.

FIG. 4 shows a cylindrical sampling device 24. The sampling device 24 comprises an analyte receiving chamber 13 in which is situated a sample chamber 23 that is likewise cylindrical. The sample chamber 23 takes the form of a passage passing through the sampling device 24 and has two openings, the first opening being the sample inlet 21. The second opening 22 is connecting by a sampling line (not shown) to a second pump 90 (not shown) to allow a flushing medium to be driven through the sample chamber 23 and out of the sample inlet 21 to flush the sample chamber 23 or to allow a medium intended for sampling to be drawn by suction through the sample inlet 21 into the interior of the sample chamber 23.

The analyte receiving chamber 13 is provided with an infeed-line passage 30 extending from the infeed line passage opening 71 to the analyte receiving chamber inlet opening 72 and an outfeed-line passage 40 extending from the analyte receiving chamber outlet opening 74 to the outfeed line passage opening 75. The sample chamber 23 is provided with a separating membrane 15. From the sample chamber 23, an analyte can diffuse through the separating membrane 15 and into the analyte receiving chamber 13.

In operation, the procedure adopted corresponds to that which was described above for the sampling device 10 shown in FIG. 1.

Figure 5:
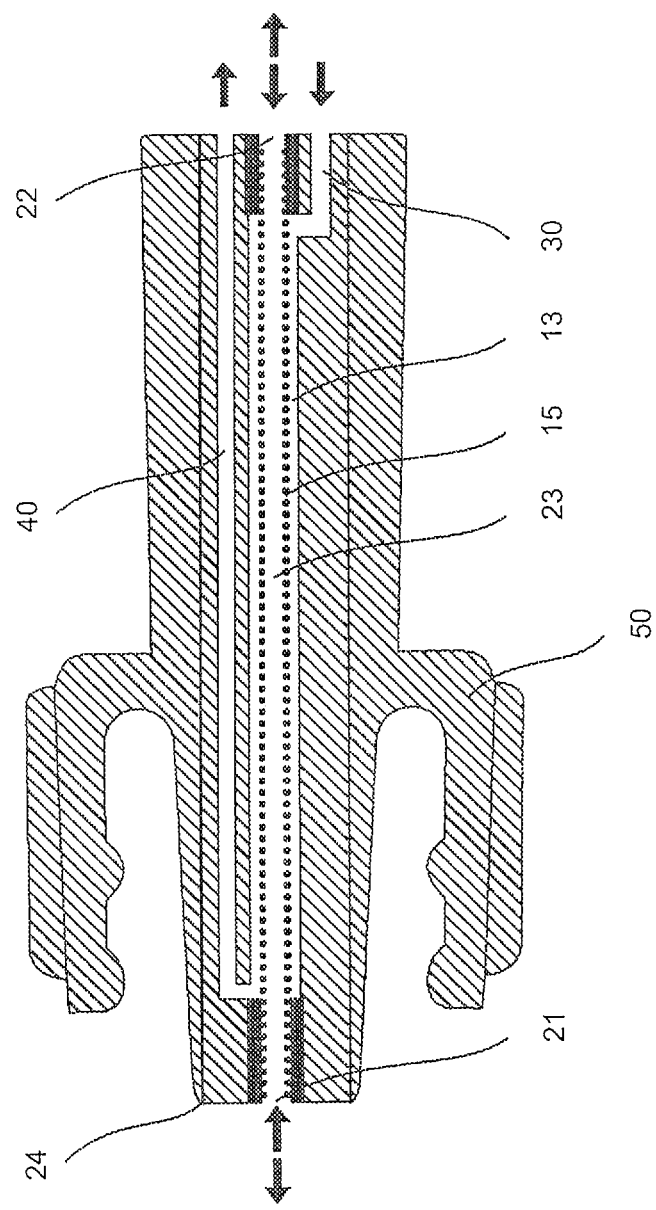
FIG. 5 is a schematic view of the exterior of a sampling device as shown in FIG. 4, when fitted with a Luer lock connector.

FIG. 5 differs from FIG. 4 only in that there is provided in this case a Luer lock connector by means of which the sampling device 24 can be connected to a sampling access by positive interengagement, a normal force and/or friction.

Figure 5A:
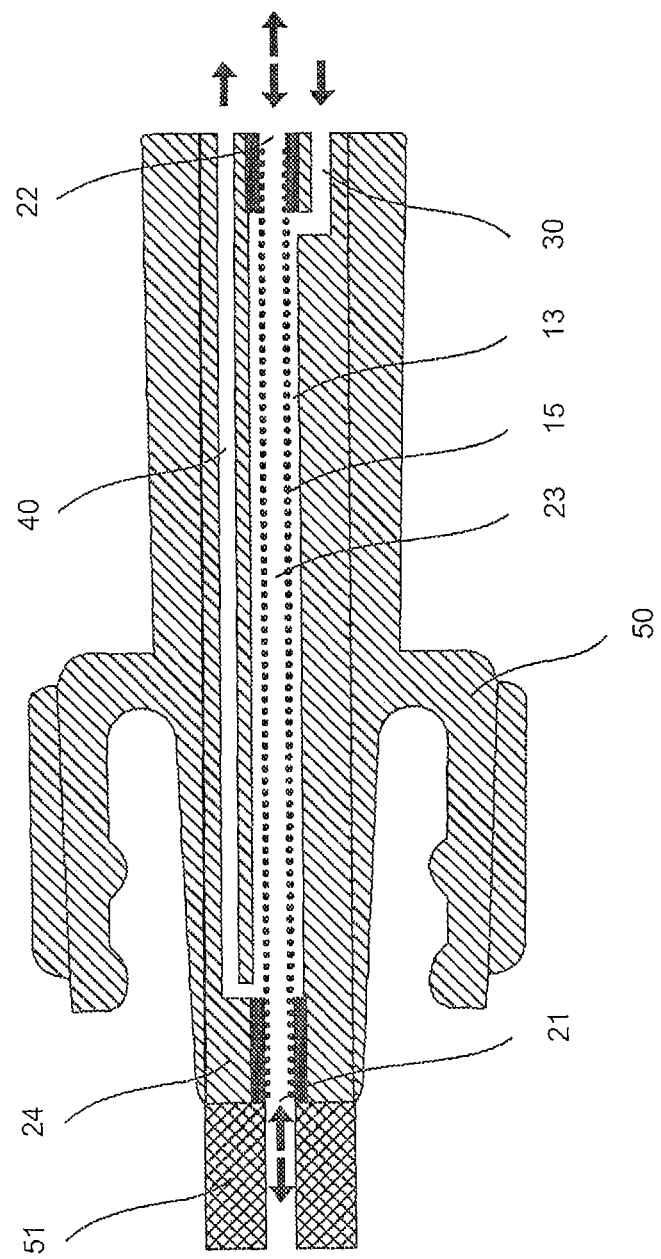
FIG. 5a is a schematic view of a further sampling device as shown in FIG. 4 having a Luer lock connector.

FIG. 5a shows a sampling device according to the invention of the kind shown in FIG. 5 that has in addition a filler body 51 to reduce a dead volume in a Luer lock connector.

FIG. 6a is a schematic view of the exterior of a sampling device 25 that is designed to be in the form of a probe. The probe has a tip that is designed in a similar way to the sampling device 10 shown in any of FIGS. 1 to 3. The cross-hatching 60 shows the approximate position of the separating membrane 15 of the sampling device 25. The infeed-line passage 30 (not shown) and outfeed-line passage 40 (not shown) of the sampling device 25 can be connected to fluid connectors (not shown). By means of a further fluid connector, a sample chamber 23 (not shown) that is formed when the sampling device 25 is put to use can be connected to a sampling line (not shown) through a connection 70.

FIG. 6b shows various possible ways of using a sampling device in conjunction with a sampling access in the form of a multilumen catheter 80. The sampling device 25 is mounted outside the multilumen catheter 80 on or in a connection 81, both the sample chambers 23, 23' and the separating membrane 15, the position of which latter is indicated by the hatched areas 60, 60', are situated outside the actual catheter and outside the main body of the medium and, when used on a human being, outside the body of the human being too. Hatched areas 61, 62 and 63 show other possible positions for the separating membrane 15 that are reached if the sampling device 25 is inserted more deeply into the multilumen catheter 80. Associated with these positions are sample inlets 21, 21a and 21b. If the separating membrane 15 is in the position indicated by the hatched area 61, the sample inlet 21 is in direct contact with the main body of the medium.

FIG. 6b also shows the use of a sampling device 25' in an outfeed line or infeed line of the multilumen catheter 80. The sampling device 25' is designed in the same way as the sampling device 25.

By the single-hatched areas 64 to 68, FIG. 6b also shows possible positions for sampling devices according to the invention (not shown, see FIG. 4 or 5 for examples) that are integrally connected to the multilumen catheter 80, its infeed lines 81, or its fluid connectors 83, or to external lines 84.

The arrangement thus enables a largely free choice to be made of the point at which samples are taken from the main body of the medium, from the multilumen catheter 80, from the latter's infeed lines and/or from its fluid connectors.

FIGS. 7a and 7b are schematic views of the use of a sampling device according to the invention in conjunction with a cannula 82, such for example as an indwelling venous cannula or an arterial cannula.

By the single-hatched areas 64, 66 and 68, FIG. 7a indicates possible positions for sampling devices according to the invention (not shown, see FIG. 4 or 5 for examples) that are integrally connected to the cannula 82, fluid connectors 83 or to external lines 84.

FIG. 7b shows various possible ways of using the sampling device 25, 25' in conjunction with a sampling access in the form of a cannula 82. Sampling device 25 is inserted in the cannula 82. The hatched area 61 shows the position of the separating medium 15 of the sampling device 25. In this arrangement the sample inlet 21 is in direct contact with the main body of the medium.

Sampling device 25', which corresponds to a sampling device 25, is inserted in a line 41 connected to the cannula 82, outside the main body of the medium intended for sampling. The hatched area 61' indicates the position of the separating medium 15 of the sampling device 25'.

Figure 8:
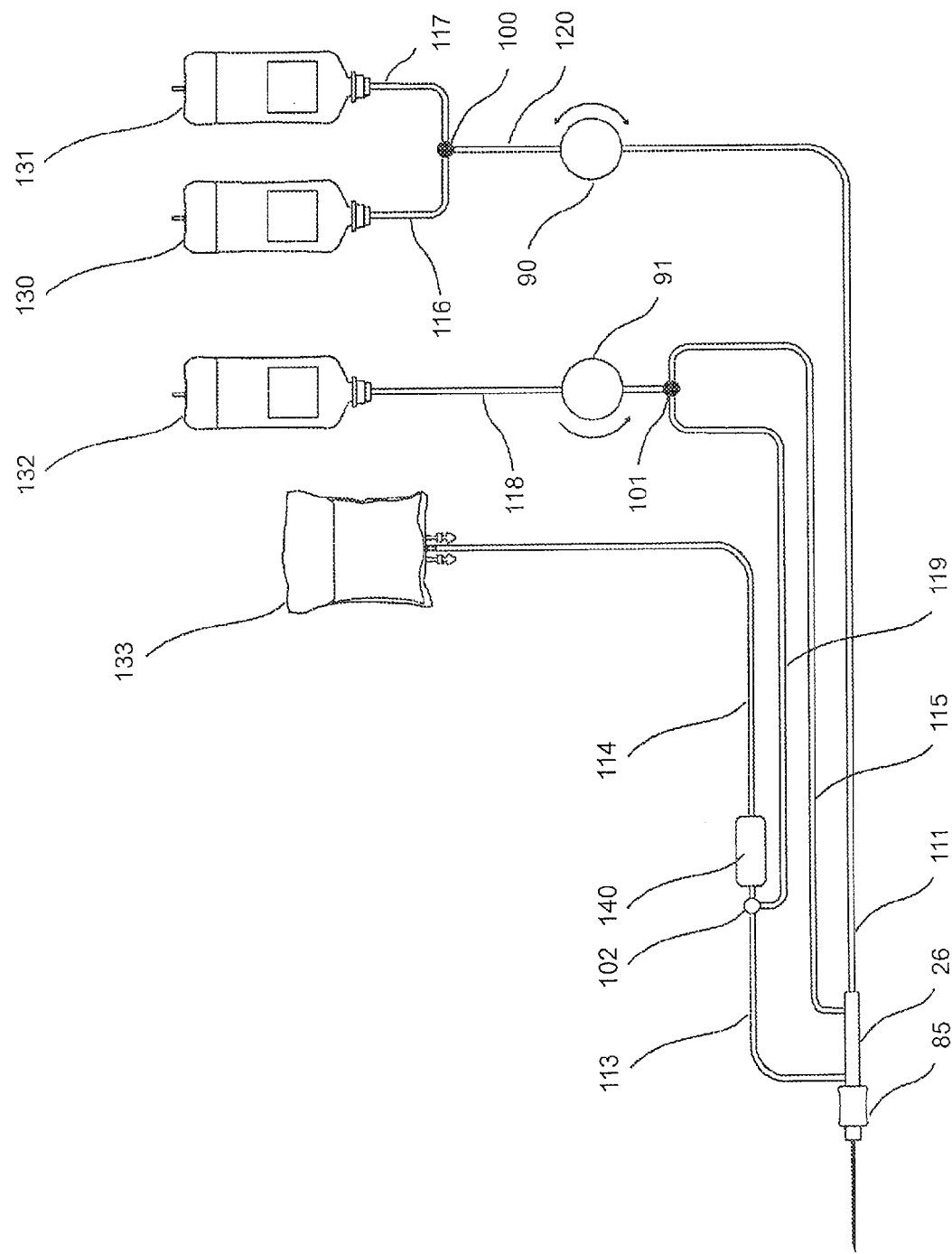
FIG. 8 is a schematic view of a sampling system according to the invention.

FIG. 8 is a schematic view of a sampling system according to the invention. A sampling access 85 is provided with a sampling device 26.

The sampling system comprises a fluidics system for samples, comprising a sampling line 111 that is connected to the sample chamber (not shown) of the sampling device 26 and that is fitted at the other end with a pump 90 that is able to pump in both directions. The other side of the pump is connected by a line 120 to a switchable connection 100 that is also connected by a line 116 to a container 130 for calibrating medium and by a line 117 to a container 131 for flushing solution. Switchable connection 100 can be switched in such a way that line 116 or line 117 or both are in fluid communication with line 120.

The sampling system also comprises a fluidics system for analysis, comprising an infeed line 115 that is in fluid communication with the infeed-line passage (not shown) of the sampling device 26 and that is fitted with a pump 91 at the other end. The other side of the pump is connected by a line 118 to a container 132 for transporting medium. The sampling system's fluidics system for analysis further comprise an outfeed line 113 that is in fluid communication with the outfeed-line passage (not shown) of the sampling device 26 and that is also connected to a sensor 140. Sensor 140 is arranged for the qualitative and/or quantitative detection of the analyte. Sensor 140 is also connected via a line 114 to a container 133 for waste medium. Infeed line 115 is also provided with a switchable connection 101 and outfeed line 113 is also provided with a connector 102. Switchable connection 101 and connector 102 are connected by a bypass line 119.

In operation, sample access 85, such for example as a cannula or catheter or the sampling access of a bioreactor, is first brought into contact with the main body of the medium. Switchable connection 100 is then set in such a way that lines 117 and 120 are in fluid communication and pump 90 is started and pumps the flushing solution from container 131 through lines 117 and 120 and sampling line 111 and into the sample chamber (not shown) of the sampling device 26. When this is done, the contents of the sample chamber (not shown) of the sampling device 26 and then the flushing solution are first conveyed into the main body of the medium (and possibly infused into the patient). Once the sample chamber (not shown) of the sampling device 26 is substantially full of flushing solution, pump 90 is stopped.

At the same time or following this, the analyte receiving chamber (not shown) of the sampling device 26 is flushed with transporting medium by switching on pump 91 and switching switchable connection 101 in such a way that pump 91 pumps transporting medium from container 132 through line 118 and infeed line 115 and into the analyte receiving chamber (not shown) of the sampling device 26 and on from there through outfeed line 113, sensor 140 and line 114 and into container 133 for waste medium. Transporting medium should usually be pumped in this case until the entire volume of material from the analyte receiving chamber (not shown) of the sampling device 26 has passed through sensor 140 and sensor 140 indicates the measured value for pure transporting medium. Pump 91 can then be stopped and, if desired, a new cycle can be started.

By reversing the direction of flow at pump 90 and starting the latter, the flushing solution is pumped towards pump 90. When this, happens, the medium intended for sampling flows into the sample chamber (not shown) of the sampling device 26, mixes there with the flushing liquid and is then pumped through the sample chamber (not shown) of the sampling device 26 and into sampling line 111, initially as a mixture with the flushing liquid and later, as the pumping continues, in a pure form. Once the sample chamber (not shown) of the sampling device 26 is substantially completely full of medium intended for sampling, pump 90 can either be stopped, as a result of which the medium intended for sampling stays in the sample chamber (not shown) of the sampling device 26 or, as an alternative to this, pump 90 may also continue to operate for a preselected time and in this way sample material can be drawn by suction into the sample chamber to ensure that there is an as constantly high a concentration of analyte as possible in the interior of the sample chamber (not shown), thus enabling as high as possible a concentration of analyte or analytes to be obtained in the analyte receiving chamber (not shown) of the sampling device 26. For the latter eventually, a volume of collecting space may also be provided in sampling line 111 for temporary storage of the medium intended for sampling. By setting switchable connection 100 in the appropriate way, the calibrating solution from container 130 may also be used for this process rather than the flushing solution. The calibrating solution may also be introduced (or infused in the case of a patient) into the main body of the medium continuously.

Once the sample chamber (not shown) of the sampling device 26 is substantially full of the medium intended for sampling, a wait is made for a preselected time to give the analyte an opportunity to diffuse into the analyte receiving chamber 13 (not shown). During the optional waiting time, the transporting medium from container 132 can either be conveyed directly to sensor 140 through bypass 119 or pump 91 can be stopped. It is also possible for further medium to be drawn continuously into the sample chamber by suction and for this medium to be expelled again only after the possibly analyte-charged transporting medium has been taken away to the sensor. And it is also possible for the medium drawn in by suction to be fed back in a loop as described above.

By means of a suitable sequence, it is also possible by this method for a medium intended for sampling to be brought into contact with the separating layer (not shown) of the sampling device 26 while enrichment and transport away are able to take place at the same time on the other side of the separating layer (not shown) of the sampling device 26. The fluidics systems on both sides may also be operated in continuous pulses or alternately.

Figure 9:
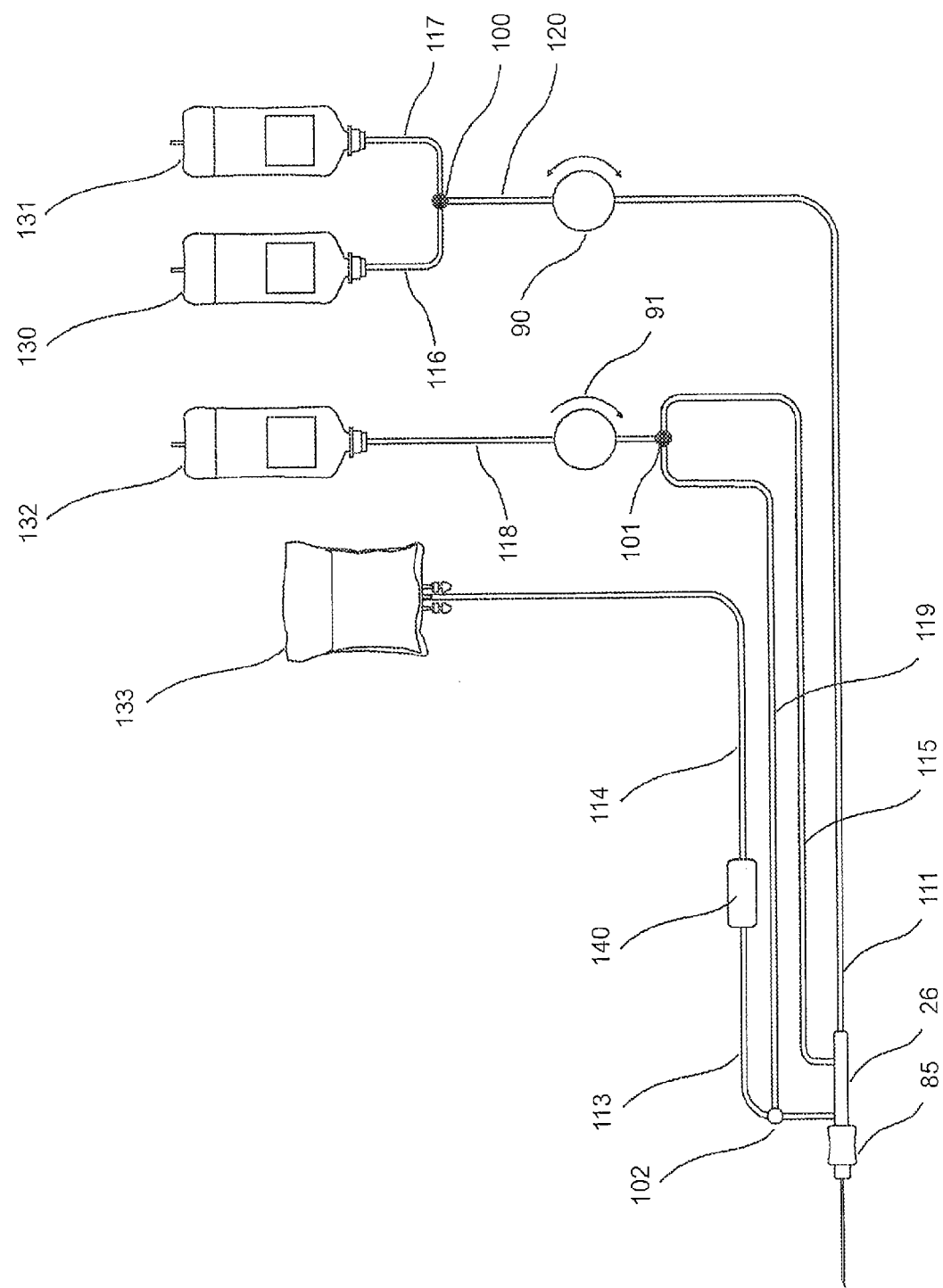
FIG. 9 is a schematic view of an alternative to the sampling system shown in FIG. 8, for longer distances between the sampling device and the sensor.

FIG. 9 is a schematic view of an alternative form of the sampling system shown in FIG. 8. In this case connector 102 is mounted very close to the sampling device 26 or is integrally connected thereto. In this way the sensor can be mounted at a greater distance from the sampling device 26. This layout is advisable if for example there are longer distances between the sampling device 26 and the sensor 140 or if there are a plurality of sampling devices 26 connected to one sensor 140.

Figure 10:
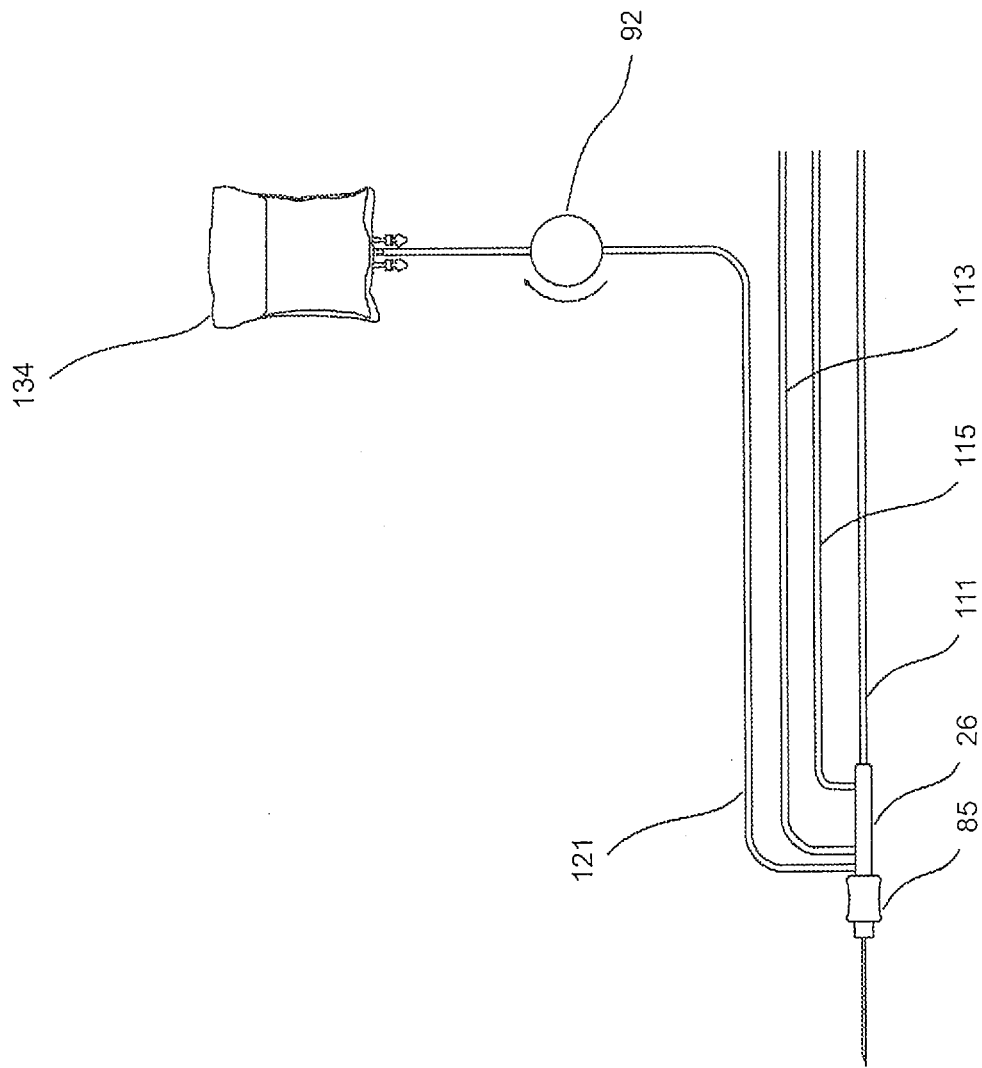
FIG. 10 is a schematic view of a further alternative to the sampling system according to the invention shown in FIG. 8, having an alternative outlet.

FIG. 10 is a schematic view of an alternative form of the sampling system shown in FIG. 8. In this case the sampling device 26 is provided in addition with an alternative outlet 121 that is in fluid communication with the sample chamber (not shown) of the sampling device 26 in the region between the sample inlet (not shown) and the separating medium (not shown) of the sampling device 26. Alternative outlet 121 is connected to pump 92 and also to container 134 for waste medium.

This enables the sample chamber (not shown) of the sampling device 26 to be flushed with calibrating medium and/or flushing medium and/or transporting medium and the medium used for flushing to be pumped away through the alternative outlet rather than into the supply of medium intended for sampling. The stress in terms of volume (of liquids) on a patient can be reduced by this means.

Figure 11:
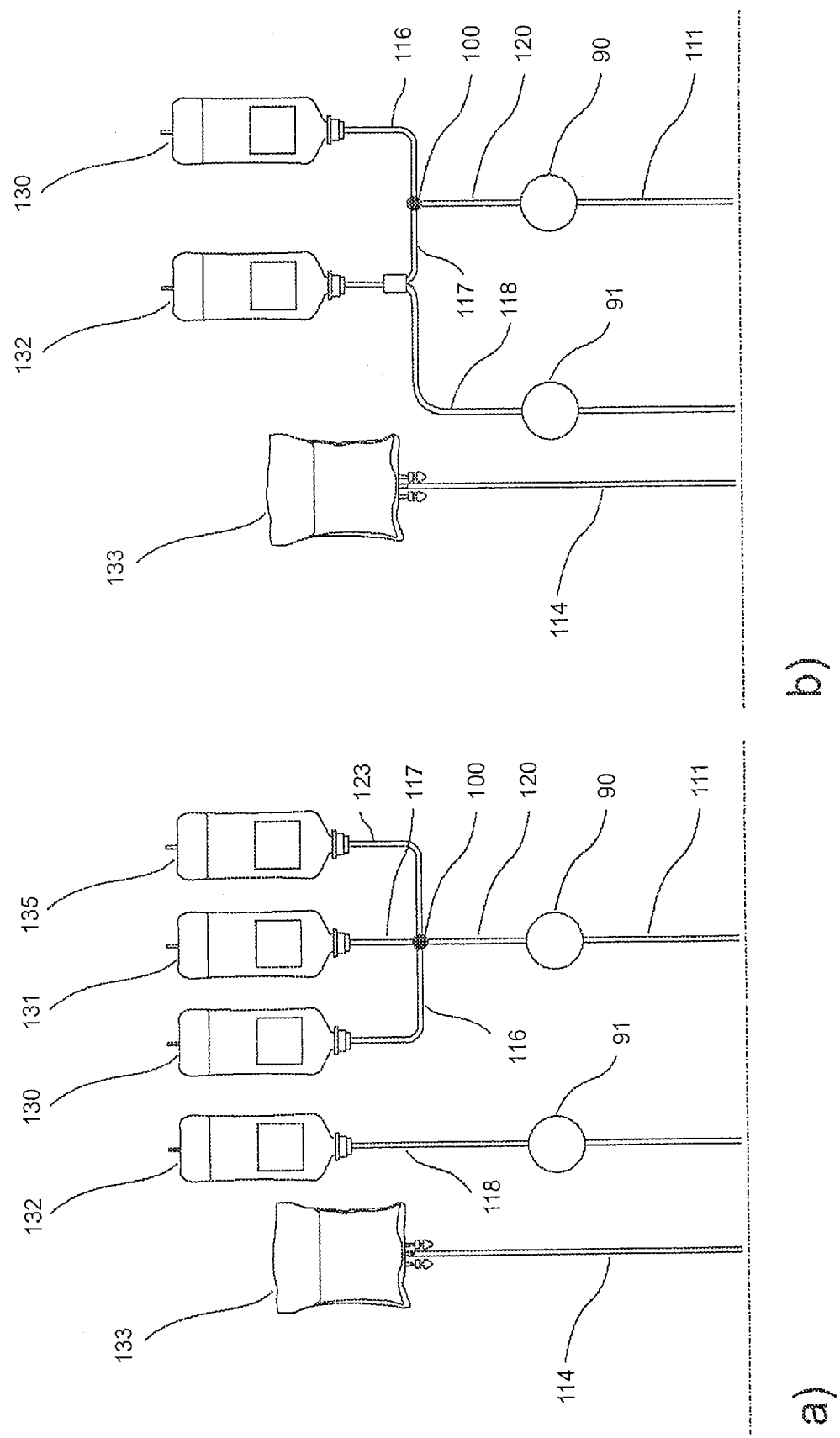
FIGS. 11a and 11b are schematic views of a further alternative to the sampling system according to the invention shown in FIG. 8, having alternative fluid storage and infeed-line systems.

FIGS. 11a and 11b are schematic views of details of the sampling system shown in FIG. 8 showing alternative fluid storage and infeed line systems.

FIG. 11a shows the construction of the fluid storage and fluid infeed-line systems when an additional container 135 is used for an additional calibrating solution. The containers 130 and 135 holding the calibrating solutions and the container 131 holding the flushing solution are connected via lines 116, 117 and 123 to the switchable connection 100, which is connected in turn to pump 90 by line 120. By means of switchable connection 100 one or others of the containers 130, 131 and 135 can be put into fluid communication with line 120. This construction is suitable for cases where a plurality of calibrating media, that contain different concentrations of the analyte for example, are used and thus for sensors that require a plurality of calibration points.

FIG. 11b shows a construction for the fluid storage and fluid infeed-line systems in which the lines for the flushing and transporting media can be united. This is a system that is particularly economical of space and that allows the sampling system to be compact and to have only a few medium containers. The transporting medium also forms the flushing medium in this case and the sampling line 111 and the infeed line are thus either connected to the supply of transporting medium and flushing medium via a switchable connection 100 as shown or are connected to one common supply container (not shown).

Figure 12:
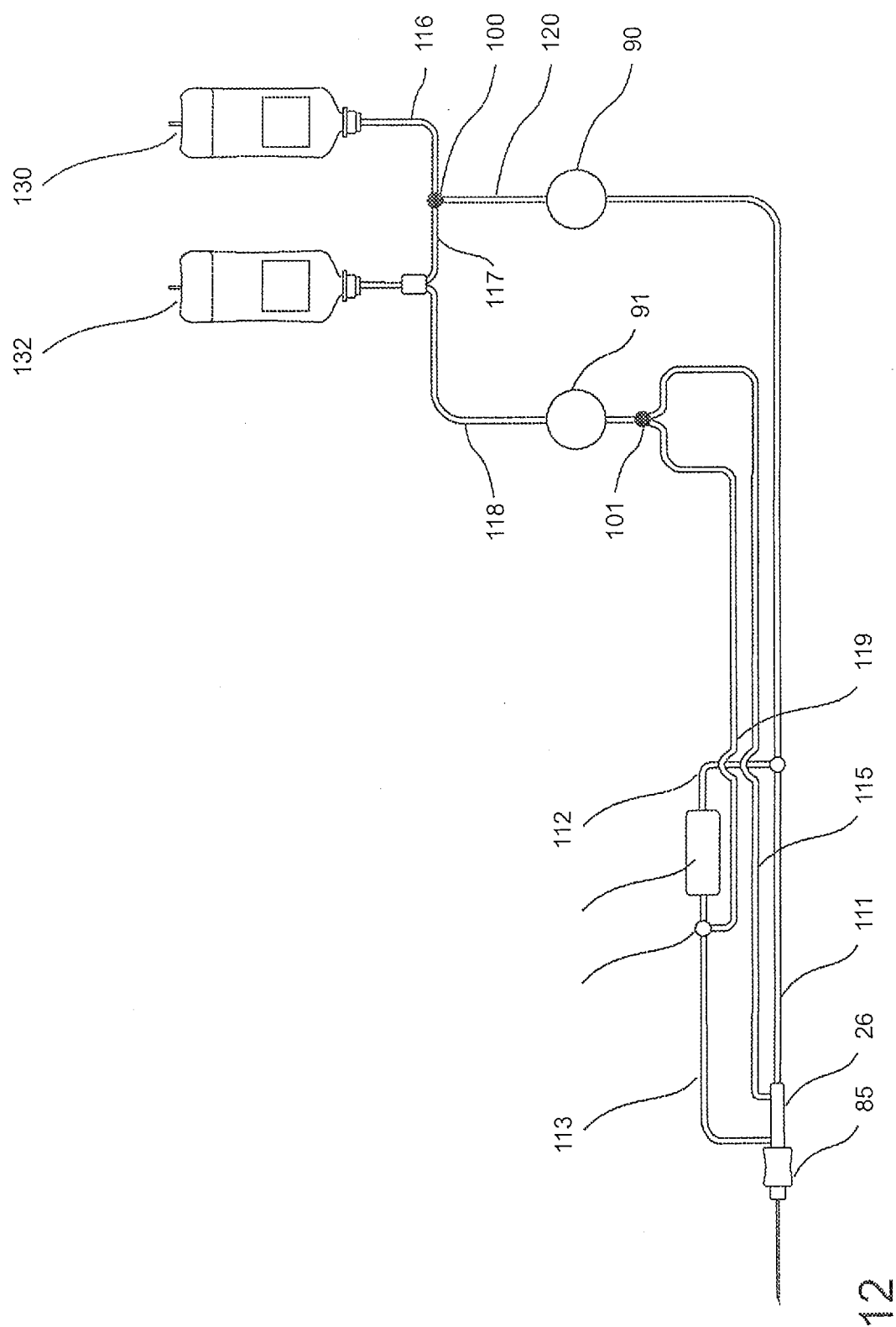
FIG. 12 is a schematic view of a further, very compact, alternative to the sampling system according to the invention shown in FIG. 8.

FIG. 12 is a schematic view of a further very compact alternative to the sampling system according to the invention shown in FIG. 8. The fluid storage and fluid infeed-line system is constructed as shown in FIG. 11b in this case. However, the container 133 for the waste medium is, in addition, omitted. The medium leaving sensor 140 after measurement is conveyed into the sampling line 111 by means of line 112 in this case. This produces a compact layout. However, the entire tubing system, the analyzing section and the media have to be of a sterile form in this case. What is preferably made available, in a pre-assembled form, is a fully enclosed sterile fluid system in, for example, cassette format. The entire sequence of operation must be set in such a way that the analyte-charged section is flushed out without falsifying the subsequent measurement.

Figure 13:
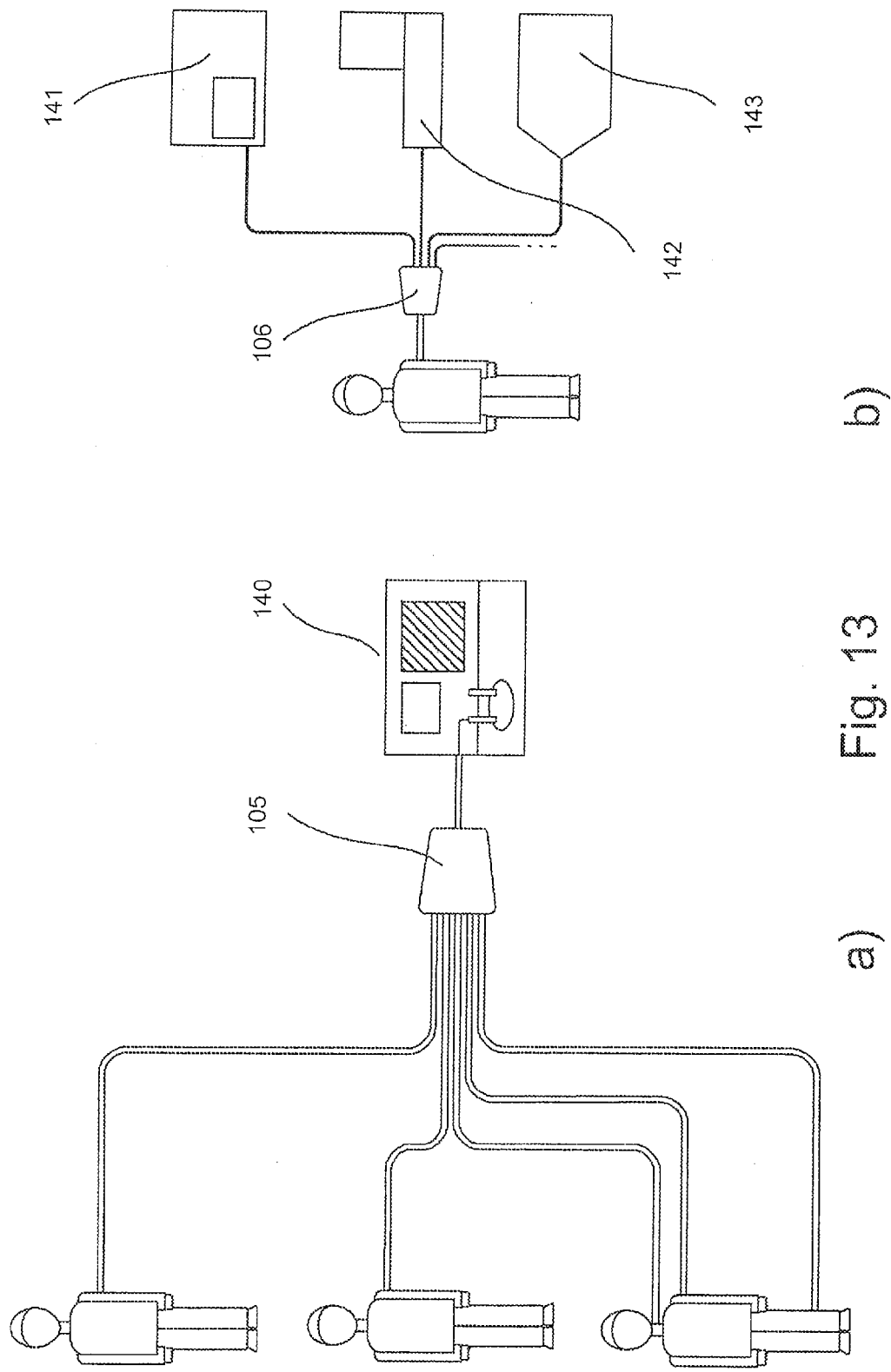
FIGS. 13a and 13b are schematic views of a sampling device according to the invention serving a plurality of patients or having a plurality of sensors or measuring stations.

FIGS. 13a and 13b are schematic views of a sampling device according to the invention serving a plurality of patients and having one sensor and of a measuring arrangement serving one patient and having a plurality of sensors. The sampling devices involved here are in principle the same as the sampling device shown in FIG. 8. FIG. 13a shows that a plurality of sampling devices 26 (not shown) in a plurality of patients and/or even a plurality of sampling devices 26 (not shown) in one patient can be connected to a single sensor 140 via a switchable connection 105. This is an obvious course to take when, for example, a method of analysis is used that is particularly costly or complicated but can be automated. FIG. 13b shows that a sampling device 26 (not shown) in one patient can be connected via a switchable connection 106 to a plurality of sensors 141, 142 and 143. This is an obvious course to take when for example different analytes need to be determined.

Figure 14:
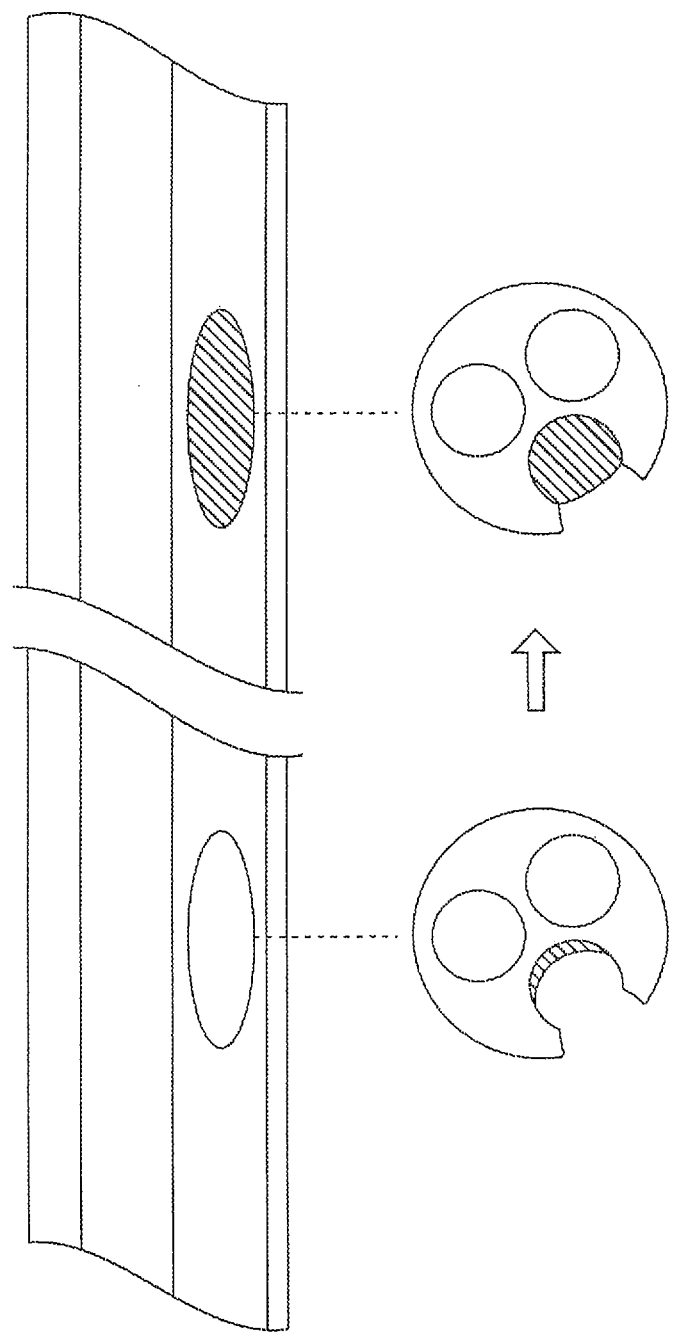
FIG. 14 is a schematic view of a catheter having an inflatable closing-off membrane.

FIG. 14 is a schematic view of a 3-lumen catheter having a catheter window to allow medium intended for sampling to enter an internal passage in the catheter. The internal passage has an internal closing-off membrane that, as a result of a medium being applied (shown on the right), causes the closing-off membrane (shown hatched) to inflate after the fashion of a balloon and thus causes a reduction in the volume of the internal passage. In the embodiment shown, the closing-off membrane is of a size such that the inflated closing-off membrane closes off (shown at top right) the catheter window to prevent a medium from passing through it.

Other embodiments of the invention are described below:

1. A sampling device for a sampling access, comprising
   an analyte receiving chamber to receive an analyte into a transporting medium, connected to an infeed-line passage and an outfeed-line passage for transporting transporting medium respectively into and out of the analyte receiving chamber,
   a sample chamber taking the form of an internal cavity, having a sample inlet to receive a sample possibly containing analyte, and
   a separating medium surrounding the internal cavity, to allow the analyte to pass through from the sample chamber into the analyte receiving chamber.

2. A sampling device as in embodiment 1, wherein the analyte receiving chamber surrounds the sample chamber.

3. A sampling device as in either of the preceding embodiments, wherein the sample chamber takes the form of a passage extending through the sampling device.

4. A sampling device as in any of the preceding embodiments, wherein the sampling device is designed for fitting to a medical sampling access and preferably to a hollow needle (cannula), catheter, port, aspirator, drain, reservoir and/or connector.

5. A sampling device as in any of the preceding embodiments, wherein the sampling device is designed for connection by positive interengagement, a normal force and/or friction to a sampling access, and preferably to a Luer lock connector and/or a screwed connector.

6. A sampling device as in any of the preceding embodiments, wherein the sampling device is designed for the arrangement of the analyte receiving chamber
   within a main body of the medium intended for sampling, through a sampling access,
   in a sampling access,
   at an end of a sampling access that is remote from a main body of the medium intended for sampling, and/or
   in a line connected to a sampling access and outside a main body of a medium intended for sampling.

7. A sampling device as in any of preceding embodiments 2 to 4, wherein the sampling device is integrally connected to the sampling access.

8. A sampling device as in any of the preceding embodiments, wherein the sampling device is designed to receive a sample of body fluid, preferably selected from blood, blood plasma, lymph, tissue fluid, cerebrospinal fluid, synovial fluid, gastric juice, gall and urine.

9. A sampling device as in any of the preceding embodiments, wherein the separating medium is a membrane.

10. A sampling device as in embodiment 9, wherein the material of the separating membrane is selected from the group comprising cellulose and derivatives thereof and in particular cellulose acetate, PTFE, polycarbonate, polypropylene, polyamides, polyesters, polyethersulfones and polysulfones.

11. A sampling device as in any of the preceding embodiments, wherein the separating medium is designed to allow the passage of an analyte selected from glucose, lactose, lactate, $Na^+$, $K^+$, $Cl^-$, $H_3O^+$, $O_2$, $CO_2$, ammonium, ammonia, methanol, ethanol, formate, acetate, glutamine, glutamate, urea, uric acid, phosphate, antibodies, growth factors, hormones, medications, and in particular narcotics and anesthetics.

12. A sampling device as in any of the preceding embodiments, wherein the inside diameter of the infeed-line passage and/or the outfeed-line passage, at the analyte receiving chamber, is from 0.2 to 0.3 mm, and preferably 0.2 to 0.3 mm, and as a particular preference 0.23 to 0.26 mm 13. A sampling device as in any of the preceding embodiments, wherein the area of that portion of the separating medium that connects the sample chamber to the analyte receiving chamber (the membrane window) is 0.5 to 350 $mm^2$, and preferably 1 to 50 $mm^2$, and as a particular preference 2 to 35 $mm^2$.

14. A sampling device as in embodiment 13, wherein the ratio of the area of the membrane window to the inside diameter of the outfeed-line passage is more than 400:1.

15. A sampling device as in any of the preceding embodiments, wherein the volume of the analyte receiving chamber is 2-50 $mm^3$.

16. A sampling device as in any of the preceding embodiments, further comprising a movable closing-off membrane for reducing and/or closing off a volume of the sample chamber or the sampling access.

17. A sampling device as in embodiment 16, further comprising a passage for controlling closing-off for exerting a pressure to move the closing-off membrane.

18. A sampling device as in any of the preceding embodiments, wherein the sample chamber further comprises an alternative outlet to allow medium received in the sample chamber to leave.

19. A sampling system, comprising
a sampling device, preferably as in any of the preceding embodiments,
a sensor connection for connecting in a sensor for detecting an analyte in a transporting medium,
an infeed line, in fluid communication with the infeed-line passage of the sampling device,
an outfeed line, in fluid communication with the outfeed-line passage of the sampling device and with the sensor connection,
a first pump to transport a medium through the outfeed line to the sensor connection.

20. A sampling system as in embodiment 19, further comprising a sampling line and, connected thereto, a second pump for pumping a sample into the sample chamber.

21. A sampling system as in either of embodiments 19 and 20, further comprising:
a supply of transporting medium and/or
a supply of calibrating medium and/or
a supply of flushing medium, that are/is in fluid communication, or can be placed in fluid communication, with the infeed line.

22. A sampling system as in any of preceding embodiments 19 to 21, wherein the first pump is arranged between (a) the supply of transporting medium and/or the supply of calibrating medium and/or the supply of flushing medium and (b) the infeed-line passage of the sampling device, to allow medium to be transported from the given supply of medium through the infeed line and into the infeed-line passage.

23. A sampling system as in any of preceding embodiments 19 to 22, further comprising a bypass line for the placing in fluid communication of the supply of transporting medium and/or the supply of calibrating medium and/or the supply of flushing medium with the sensor connection, without the medium passing through the analyte receiving chamber of the sensor device.

24. A sampling system as in embodiment 23, further comprising a switchable connection for the placing in fluid communication of the bypass line with the outfeed line.

25. A sampling system as in either of preceding embodiments 23 and 24, further comprising a switchable connection for the alternative placing in fluid communication of the supply of transporting medium and/or the supply of calibrating medium and/or the supply of flushing medium with either the infeed line or the bypass line.

26. A sampling system as in any of preceding embodiments 19 to 25, further comprising an outflow line for the placing in fluid communication of the outfeed line with the sampling line via the sensor connection and possibly via a sensor.

27. A sampling system as in embodiment 26, further comprising a switchable connection for the alternative placing in fluid communication
(a) of the outfeed line with the outflow line, via a sensor if required, or
(b) of the outfeed line with a waste line, via a sensor if required, to convey medium leaving the outfeed line, through the sensor if required, to a means of disposing of medium.

28. A sampling system as in any of embodiments 19 to 27, further comprising a switchable connection for connecting the supply of transporting medium and/or the supply of calibrating medium and/or the supply of flushing medium to the sampling line via the second pump.

29. A sampling system as in any of preceding embodiments 19 to 28, further comprising a control system, connected to the second pump, to control the second pump in such a way that
Step 1: a sample is drawn by suction into the sample chamber,
Step 2: the sample that was drawn in is present in the sample chamber for a preselected time and then
Step 3: the sample that was drawn in is expelled from the sample chamber.

30. A sampling system as in embodiment 29, further comprising a hollow needle, the analyte receiving chamber being arranged in the hollow needle.

31. A sampling system as in either of preceding embodiments 29 and 30, wherein the control system is also connected to the first pump to control the latter in such a way that, in step 2:

Step a: transporting medium is present in the analyte receiving chamber for a preselected time and then Step b: transporting medium possibly containing analyte is transported from the analyte receiving chamber into the outfeed-line passage.

32. A sampling system as in any of preceding embodiments 29 to 31, wherein the control system is also arranged to control the first pump in such a way that Step c: after step b) transporting medium possibly containing analyte is transported from the outfeed-line passage to the sensor connection.

33. A sampling system comprising
a hollow needle,
a sampling device having an analyte receiving chamber in fluid communication between an infeed line and an outfeed line, the analyte receiving chamber having an opening that is closed off by a membrane permeable to analyte to allow the analyte to pass through from a region outside the analyte receiving chamber into the analyte receiving chamber, and the analyte receiving chamber being arranged in the hollow needle,
a first pumping device to transport a transporting medium through the analyte receiving chamber,
a second pumping device to draw in by suction and, as an option, to expel a medium intended for analysis through the hollow needle, and
a control system in operative connection with the first pumping device, the control system being arranged to cause the transporting medium to be pumped through the analyte receiving chamber at a preselected time to allow a sample of the transporting medium possibly containing analyte to be obtained.

34. A sampling system as in any of preceding embodiments 19 to 33, further comprising, in fluid communication with the sensor connection, a sensor arranged to determine an analyte selected from glucose, lactose, lactate, $Na^+$, $K^+$, $Cl^-$, $H_3O^+$, $O_2$, $CO_2$, ammonium, ammonia, methanol, ethanol, formate, acetate, glutamine, glutamate, urea, uric acid, phosphate, antibodies, growth factors, hormones, medications, and narcotics and anesthetics.

35. A method of sampling comprising the following steps:
1) drawing by suction of a sample into a sample chamber of a sampling device as in any of embodiments 19 to 34, the interior of the hollow, needle of a sampling system as in embodiment 33 possibly forming the sample chamber,
2) making available of a transporting medium in the analyte receiving chamber for a preselected time to allow an analyte possibly contained in the sample to enter the analyte receiving chamber,
3) expulsion of the sample that was drawn into the sample chamber, and
4) before, simultaneously with, or after step 3), transport of transporting medium out of the analyte receiving chamber.

36. A method of sampling as in embodiment 35, further comprising the step of: flushing the analyte receiving chamber and/or the sensor with analyte-free transporting medium, flushing medium or calibrating medium.

37. A method of sampling as in either of preceding embodiments 35 and 36, further comprising the step of: applying a calibrating medium to the analyte receiving chamber by feeding the calibrating medium into the analyte receiving chamber through the infeed-line passage.

38. A method of sampling as in any of preceding embodiments 35 to 37, further comprising the step of: producing a calibrated concentration of an analyte in the analyte receiving chamber by
1. feeding the calibrating medium into the sample chamber and
2. allowing analyte to pass through into a transporting medium in the analyte receiving chamber for a preselected period of time.

39. A method of sampling as in embodiment 38, further comprising the step of:
allowing the calibrating medium to leave through an alternative outlet of the sampling device.

40. A method of analysis comprising the following steps: carrying out of a method of sampling as in any of preceding embodiments 35 to 39, the transporting medium possibly containing analyte being transported in step 4) to a sensor for determining the analyte.

The invention claimed is:

1. A sampling device for a sampling access to detect the presence of analyte in a sample, comprising:
a sample chamber taking the form of an internal cavity enclosed within the sampling device, wherein the sample chamber includes a first opening in a first end of the sampling device, said first opening being a sample inlet to receive a sample and a second opening at a second end of the sampling device opposite said first end;
an analyte receiving chamber enclosed within the sampling device and surrounding a portion of the sample chamber;
a separating medium defining an interface between the sample chamber and the analyte receiving chamber, the separating medium adapted to allow the analyte to pass through from the sample chamber into the analyte receiving chamber;
an infeed line passage extending from an infeed line passage opening in the second end of the sampling device to an analyte receiving chamber inlet opening; and
an outfeed line passage extending from an analyte receiving chamber outlet opening to an outfeed line passage opening in the second end of the sampling device,
wherein said sampling device is adapted so that fluid fed into the infeed line passage opening flows into a first end of the analyte receiving chamber, then along the length of the analyte receiving chamber to a second end of the analyte receiving chamber, before flowing into the outfeed line passage and exiting through the outfeed line passage opening.

2. The sampling device of claim 1, wherein a cross-section of the sampling device where the analyte receiving chamber surrounds the sample chamber includes a ring-shaped analyte receiving chamber surrounding a circular sample chamber separated by a ring-shaped separating medium.

3. The sampling device of claim 1, wherein the first end of the analyte receiving chamber is located at the second end of the sampling device and the second end of the analyte receiving chamber is located at the first end of the sampling device.

4. The sampling device of claim 1, wherein at least one of:
the sample chamber takes the form of a passage extending through the sampling device
the sampling device is designed for fitting to a medical sampling access that includes at least one of a hollow needle, a cannula, a catheter, a port, an aspirator, a drain, a reservoir and a connector, and the sampling device is designed for connection by positive interengagement, a normal force and/or friction to the medical sampling access.

5. The sampling device of claim 1, wherein the sampling device is integrally connected to the sampling access.

6. The sampling device of claim 1, wherein at least one of:
the sampling device is designed to receive the sample that is selected from at least one of blood, blood plasma, lymph, tissue fluid, cerebrospinal fluid, synovial fluid, gastric juice, gall and urine, and
the separating medium is designed to allow the passage of the analyte selected from glucose, lactose, lactate, $Na^+$, $K^+$, $Cl^-$, $H_3O^+$, $O_2$, $CO_2$, ammonium, ammonia, methanol, ethanol, formate, acetate, glutamine, glutamate, urea, uric acid, phosphate, antibodies, growth factors, hormones, medications, and narcotics and anesthetics.

7. The sampling device of claim 1, wherein the separating medium is a membrane and the material of the membrane is selected from the group comprising cellulose and derivatives thereof that include at least one of cellulose acetate, PTFE, polycarbonate, polypropylene, polyamides, polyesters, polyethersulfones and polysulfones.

8. The sampling device of claim 1, wherein at least one of:
the inside diameter of the infeed-line passage and/or the outfeed-line passage, at the analyte receiving chamber, is from 0.01 to 2 mm, and
the interface of the separating medium that connects the sample chamber to the analyte receiving chamber is has an area from 0.5 to 350 $mm^2$.

9. The sampling device as claimed in claim 1, wherein at least one of:
the inside diameter of the infeed-line passage and/or the outfeed-line passage, at the analyte receiving chamber, is from 0.25 to 0.5 mm, and/or
the interface of the separating medium that connects the sample chamber to the analyte receiving chamber has an area from 1 to 50 $mm^2$.

10. The sampling device as claimed in claim 1, wherein at least one of:
the inside diameter of the infeed-line passage and/or the outfeed-line passage, at the analyte receiving chamber, is from 0.23 to 0.26 mm, and
the interface of the separating medium that connects the sample chamber to the analyte receiving chamber has an area from 2 to 35 $mm^2$.

11. The sampling device of claim 5, wherein the sampling access comprises at least one medical sampling access selected from the group consisting of a hollow needle, a cannula, a catheter, a port, an aspirator, a drain, a reservoir, and a connector.

12. A sampling system, comprising
the sampling device of claim 1,
a sensor connection for connecting a sensor for detecting analyte in a transporting medium,
an infeed line, in fluid communication with the infeed-line passage of the sampling device,
an outfeed line, in fluid communication with the outfeed-line passage of the sampling device and with the sensor connection,
a first pump to transport a medium through the outfeed line to the sensor connection.

13. The sampling system of claim 12, further comprising:
a supply of transporting medium and/or
a supply of calibrating medium and/or
a supply of flushing medium,
that are/is in fluid communication, or can be placed in fluid communication, with the infeed line.

14. The sampling system of claim 13, wherein the first pump is arranged between (a) the supply of transporting medium and/or the supply of calibrating medium and/or the supply of flushing medium and (b) the infeed-line passage of the sampling device, to allow medium to be transported from the given supply of medium through the infeed line into the infeed-line passage, and further comprising a control system connected to the first pump, to control the latter in such a way that:
Step a: transporting medium is present in the analyte receiving chamber for a preselected time and then
Step b: transporting medium is transported from the analyte receiving chamber into the outfeed-line passage.

15. The sampling system of claim 12, further comprising a control system, connected to the second pump, to control the second pump in such a way that
Step 1: the sample is drawn by suction into the sample chamber,
Step 2: the sample that was drawn in is present in the sample chamber for a preselected time and then
Step 3: the sample that was drawn in is expelled from the sample chamber,
the control system being so arranged that the first pump is controlled in such a way that, in step 2:
Step a): transporting medium is present in the analyte receiving chamber for a preselected time and then
Step b): transporting medium is transported from the analyte receiving chamber into the outfeed-line passage.

16. The sampling system of claim 12, further comprising at least one of:
in fluid communication with the sensor connection, a sensor arranged to determine an analyte selected from glucose, lactose, lactate, $Na^+$, $K^+$, $Cl'$, $H30^+$, $O2$, $CO2$, ammonium, ammonia, methanol, ethanol, formate, acetate, glutamine, glutamate, urea, uric acid, phosphate, antibodies, growth factors, hormones, medications, and narcotics and anesthetics, and
the sampling system being designed to receive the sample selected from blood, blood plasma, lymph, tissue fluid, cerebrospinal fluid, synovial fluid, gastric juice, gall and urine, and
the sampling system further comprising a bypass line for the placing in fluid communication of the supply of transporting medium and/or the supply of calibrating medium and/or the supply of flushing medium with the sensor connection, without the medium passing through the analyte receiving chamber of the sensor device.

17. The sampling system of claim 12, further comprising a sampling line and, connected thereto, a second pump for pumping the sample into the sample chamber.

18. A sampling device to detect the presence of analyte in a sample, comprising
a hollow needle comprising:
a sample chamber taking the form of an internal cavity enclosed within the hollow needle, wherein the sample chamber includes a first opening in a first end of the hollow needle, said first opening being a sample inlet to receive a sample and a second opening at a second end of the sampling device opposite said first end;

an analyte receiving chamber enclosed within the hollow needle and surrounding a portion of the sample chamber;
a separating medium defining an interface between the sample chamber and the analyte receiving chamber, the separating medium adapted to allow the analyte to pass through from the sample chamber into the analyte receiving chamber;
an infeed line passage extending from an infeed line passage opening in the second end of the hollow needle to an analyte receiving chamber inlet opening; and
an outfeed line passage extending from an analyte receiving chamber outlet opening to an outfeed line passage opening in the second end of the hollow needle,
wherein said sampling device is adapted so that fluid fed into the infeed line passage opening flows into a first end of the analyte receiving chamber, then along the length of the analyte receiving chamber to a second end of the analyte receiving chamber, before flowing into the outfeed line passage and exiting through the outfeed line passage opening.

* * * * *

UNITED STATES PATENT AND TRADEMARK OFFICE
CERTIFICATE OF CORRECTION

PATENT NO. : 10,022,081 B2
APPLICATION NO. : 13/256184
DATED : July 17, 2018
INVENTOR(S) : Wolfgang Künnecke Page 1 of 1

It is certified that error appears in the above-identified patent and that said Letters Patent is hereby corrected as shown below:

In the Claims

In Column 29, Line 36 of Claim 9 reads "is from 0.25 to 0.5 mm, and/or" but should read "is from 0.25 to 0.5 mm, and"

In Column 30, Line 39 of Claim 16 reads "glucose, lactose, lactate, $Na^+$, $K^+$, $Cl^-$, $H3O^+$, $O_2$, $CO_2$," but should read "glucose, lactose, lactate, $Na^+$, $K^+$, $Cl^-$, $H_3O^+$, $O_2$, $CO_2$,"

Signed and Sealed this
Twentieth Day of November, 2018

Andrei Iancu
*Director of the United States Patent and Trademark Office*